(12) United States Patent
Royaee

(10) Patent No.: US 10,636,519 B2
(45) Date of Patent: *Apr. 28, 2020

(54) METHOD AND DEVICE FOR IDENTIFICATION AND/OR SORTING OF MEDICINES

(71) Applicant: Atabak R. Royaee, Ridgefield, CT (US)

(72) Inventor: Atabak R. Royaee, Ridgefield, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/947,779

(22) Filed: Apr. 7, 2018

(65) Prior Publication Data

US 2018/0301212 A1 Oct. 18, 2018

Related U.S. Application Data

(63) Continuation of application No. 14/555,605, filed on Nov. 27, 2014, now Pat. No. 9,940,439.

(60) Provisional application No. 61/910,283, filed on Nov. 29, 2013.

(51) Int. Cl.
| | |
|---|---|
| *G16H 20/13* | (2018.01) |
| *B07C 5/38* | (2006.01) |
| *B07C 5/342* | (2006.01) |
| *G06F 19/00* | (2018.01) |
| *H04N 7/18* | (2006.01) |
| *G06K 9/00* | (2006.01) |
| *G06K 9/62* | (2006.01) |
| *B65D 83/04* | (2006.01) |

(52) U.S. Cl.
CPC .......... *G16H 20/13* (2018.01); *B07C 5/3422* (2013.01); *B07C 5/38* (2013.01); *G06F 19/00* (2013.01); *G06F 19/3462* (2013.01); *G06K 9/00* (2013.01); *G06K 9/6202* (2013.01); *G06K 9/6203* (2013.01); *H04N 7/188* (2013.01); *B65D 83/04* (2013.01)

(58) Field of Classification Search
CPC ......... B07C 5/10; B07C 5/126; B07C 5/3422; B07C 5/342; B07C 5/362; B07C 5/367; B07C 5/368; B07C 5/38; G06F 19/34; G06F 19/3456; G06F 19/3462; B65D 83/04

See application file for complete search history.

(56) References Cited

U.S. PATENT DOCUMENTS

| | | | | |
|---|---|---|---|---|
| 5,085,510 A * | 2/1992 | Mitchell | ............... | B07C 5/3422 209/577 |
| 7,417,203 B2 * | 8/2008 | Lofquist | ................ | B07C 5/365 209/44.2 |

(Continued)

FOREIGN PATENT DOCUMENTS

| | | | |
|---|---|---|---|
| JP | 10035626 A | * | 2/1998 |
| JP | 10035626 A | | 2/1998 |

(Continued)

*Primary Examiner* — John Villecco

(57) ABSTRACT

A medicine identification and sorting system is disclosed, which includes an image capturing system for creating a digital image of at least a portion of a target medicine, and an image processing system for comparing said created target medicine image with reference medicine images in a reference medicine image database to identify and/or then sort the medicine from a mixture of medicines.

16 Claims, 21 Drawing Sheets

(56) References Cited

U.S. PATENT DOCUMENTS

| | | | | |
|---|---|---|---|---|
| 7,516,836 B2* | 4/2009 | Trygar | ................... | B65B 5/103 198/392 |
| 8,948,508 B2* | 2/2015 | Zheng | ................... | G06K 9/00 382/162 |
| 9,111,357 B2* | 8/2015 | Brossette | ............ | G06K 9/4638 |
| 9,824,297 B1* | 11/2017 | Guan | ................ | G06K 9/00335 |
| 9,842,257 B2* | 12/2017 | Gershtein | ................ | G06K 9/00 |
| 9,846,566 B1* | 12/2017 | Kapadia | ................... | G06F 7/06 |
| 2005/0224510 A1* | 10/2005 | Remis | ................... | B65B 5/103 221/69 |
| 2008/0190953 A1* | 8/2008 | Mallett | ................... | A61L 11/00 221/13 |
| 2010/0041937 A1* | 2/2010 | Gonzalez | ............ | B09B 3/0075 588/321 |
| 2012/0096816 A1* | 4/2012 | Shail | ................... | B65B 5/103 53/473 |
| 2012/0163685 A1* | 6/2012 | Rothschild | ........... | G06F 19/326 382/128 |
| 2012/0290619 A1* | 11/2012 | DeLise, Jr. | .......... | G06F 19/326 707/776 |
| 2012/0330684 A1* | 12/2012 | Jacobs | ................... | H04N 7/18 705/3 |
| 2013/0202184 A1* | 8/2013 | Grove | ................... | G07D 5/00 382/136 |
| 2013/0226600 A1* | 8/2013 | Barfield | ................ | G06Q 50/22 705/2 |
| 2014/0025199 A1* | 1/2014 | Berg | ................... | G07F 11/005 700/232 |
| 2014/0214199 A1* | 7/2014 | Utech | ................... | G06F 17/00 700/236 |
| 2014/0355849 A1* | 12/2014 | Brossette | ............ | G06F 19/3462 382/128 |
| 2015/0046177 A1* | 2/2015 | Nozawa | .............. | G06F 19/3456 705/2 |
| 2015/0170373 A1* | 6/2015 | Yonaha | ................... | G06K 9/00 382/143 |
| 2015/0178674 A1* | 6/2015 | Yonaha | ................... | G06Q 50/22 705/2 |
| 2015/0266654 A1* | 9/2015 | Baarman | ........... | B65D 83/0409 221/190 |
| 2015/0302255 A1* | 10/2015 | Gershtein | ................ | G06K 9/00 382/128 |
| 2015/0317534 A1* | 11/2015 | Brossette | ............ | G06K 9/4638 348/207.1 |
| 2016/0167866 A1* | 6/2016 | Omura | ................... | B65B 35/06 221/173 |
| 2016/0193113 A1* | 7/2016 | Jacobs | ................... | B65D 83/04 |
| 2017/0132867 A1* | 5/2017 | Berg | ................... | G07F 11/005 |
| 2017/0140601 A1* | 5/2017 | Kohama | ................... | G06T 7/70 |
| 2017/0224587 A1* | 8/2017 | Koike | ................... | A61J 7/0084 |
| 2017/0246083 A1* | 8/2017 | Amano | ................... | A61J 3/00 |
| 2017/0264867 A1* | 9/2017 | Amano | ............. | G01N 21/9508 |
| 2017/0270274 A1* | 9/2017 | Garcia | ................. | A61J 7/0481 |

FOREIGN PATENT DOCUMENTS

| | | | | |
|---|---|---|---|---|
| WO | 2011112606 A1 | 9/2011 | | |
| WO | WO-2011112606 A1 * | 9/2011 | ................ | A61J 7/04 |

* cited by examiner

METHOD AND DEVICE FOR IDENTIFICATION AND/OR SORTING OF MEDICINES

CROSS-REFERENCE TO RELATED APPLICATION

This application claims priority to U.S. application Ser. No. 14/555,605, filed Nov. 27, 2014, now U.S. Pat. No. 9,940,439, which claims the benefit of U.S. Provisional Application No. 61/910,283 filed Nov. 29, 2013, the entire disclosure of each of which is hereby incorporated herein by reference.

FIELD

The subject technology relates to a system as well as to a method and device for identifying and/or sorting mixed medicines of different types for proper disposal.

BACKGROUND

Every year, a large percentage of medicines (including prescription and over-the-counter) sold remain unused in households or hospitals, are recalled or become expired. For example, in one county (King county, WA) in the U.S., the amount of unused household medicines adds up to about 11 million containers per year. Unwanted medicines that aren't properly disposed of end up in the environment. Currently, the two main modes of disposing of unused medicines are by flushing them down the toilet or throwing them in trash. Both of these methods contribute to the contamination of soil and the underground or surface water supplies. Wastewater treatment processes do not remove pharmaceuticals contained in medicines. Most pharmaceuticals are not biodegradable and thus exposure to air or sun in landfills does not deactivate or degrade them. As the results, these chemicals accumulate in the environment and in aggregate can be hazardous to the environment and human health. For instance, an Associate Press investigation has found that in 24 major metropolitan cities (hosted.ap.org/specials/interactives/pharmawater_site/) in the U.S. the drinking water supplies of at least 46 million people are contaminated with minute amounts of many pharmaceuticals. Some of frequently detected pharmaceuticals in this investigation were atenolol (heart medication), carbamazepine (for seizure), gemfibrozil (anti-cholesterol), meprobamate (tranquilizer), naproxen (over-the-counter pain reliever), phenytoin (anti-seizure medication), sulfamethoxazole and trimethoprinm (antibiotics).

At the moment, there is no way of knowing what impact low levels of pharmaceuticals will have on human health. However, there is no doubt that a cumulative effect of so many different drugs (including anti-psychotic drugs, antibiotics, pain medications, heart and circulation drugs, contraceptive drugs, diabetes drugs, and chemotherapeutic or anti-proliferative drugs) can have adverse effect on human health. Therefore, there remains a need for a safe and proper disposal of medicines.

SUMMARY

The first step in proper disposal of medicines is a proper separation. The subject technology provides a method and a device for effective identification and separation of medicines when these medicines are not in their original containers and are loose and mixed with other types of medicines.

The balk of almost all medicines is made up of excipients, or inactive substances that are formulated alongside the active pharmaceutical ingredient (API or AI). In general, excipients are substantially less harmful than APIs. The most environmentally effective means for proper disposal of medicines therefore includes first separating excipients from APIs and then properly disposing of the APIs by incineration, recycling, chemical modification or the like. Thus, the first step in proper disposal of medicines is their proper identification and/or separation. Separated medicines can then be subject to further processing for isolating their active ingredients.

The majority of the unused medicines and medications that eventually find their ways into the environment are in form of medicines or oral dosage forms (e.g., syrups). Oral dosage forms are usually the most convenient choice for taking medicines. As known worldwide, taking a medicine via oral route is one of the best options as it's the simplest and easiest way for any patient to take a medication. Other frequently used forms of medicines are injectables (e.g., ampules), suppositories and inhalers. As such, there exists a need for a system and method for rapid identification and/or sorting of dosage forms of different physical attributes and characteristics such as size, shape, color, etc.

Thus, in one aspect, the subject technology relates to a medicine identification system that can identify and/or sort a target medicine from a mixture of medicines; including: (a) an image capturing system for creating a digital image of an least a portion of a target medicine and (b) an image processing system for comparing said target medicine image with reference medicine images in a reference medicine image database. In an embodiment relating to this aspect, the image capture system and said image processing system further includes a handheld electronic device.

In another aspect, the subject technology relates to a medicine identification system that can identify and/or sort a target medicine from a mixture of medicines; including: (a) an image capturing system for creating a digital image of an least a portion of a target medicine; (b) an image processing system for comparing said target medicine image with reference medicine images in a reference medicine image database; and (c) a sorting system having a medicine identification chamber and sorting elements for routing said target medicine from said identification chamber to a desired location after said target medicine image is processed or identified. In an embodiment relating to this aspect, the image capturing system, said image processing system and said sorting system include a handheld or portable device.

In another aspect, the subject technology relates to a medicine identification system that can identify and/or sort a target medicine from a mixture of medicines; including: (a) a first sorting system for sorting medicines based on their width or diameter as they move radially within a sorter of the first sorting system; (b) an image capturing system for creating a digital image of an least a portion of a target medicines; (c) an image processing system for comparing said target medicine image with reference medicine images in a reference medicine image database; and (d) a second sorting system having a medicine identification chamber and sorting elements for routing said target medicine from said identification chamber to a desired location after said target medicine image is processed or identified.

In another aspect, the subject technology relates to a method for identifying and sorting a target medicine from a mixture of medicines including an image capturing step for creating at least one digital image of the target medicine, an image processing step for comparing the at least one digital image with reference images and identifying the target medicine by determining a match between the at least one digital image and a reference image, and a sorting step for routing said target medicine to a desired location after the target medicine is processed or identified.

In an embodiment relating to any of the above aspects, the method further includes a first queuing and/or sorting step for queuing or sorting of the mixture of medicines before or during their introduction into the image-capturing step. Alternatively or in addition, the first queuing and/or sorting step is performed by a first sorting apparatus, the image capturing step is performed by an image capturing apparatus, the image processing step is performed by an image processing apparatus, and the sorting step is performed by a second sorting apparatus. Alternatively or in addition, said first queuing and/or sorting step arrange the medicines such that they are introduced one-by-one to the image capture step. Alternatively or in addition, the first queuing and/or sorting apparatus include a plurality of ramps designed to engage with and route the medicines towards the image capturing apparatus.

Alternatively or in addition, the image capturing apparatus includes a digital camera. Alternatively or in addition, the image processing apparatus includes a central processing unit, a main memory, and a storage unit; wherein the storage unit further comprises a database of the reference images comprising digital images of at least a portion of reference medicines. Alternatively or in addition, the second sorting apparatus includes flapper elements controlled by electric motors. Alternatively or in addition, the determining of a match between the at least one digital image and the reference images is based on a match probability output or percent identity between the at least one digital image and the reference images.

Alternatively or in addition, the reference images includes images of known medicines produced under a similar condition as the target medicine. Alternatively or in addition, the comparing of the at least one digital image with the reference images include comparing of at least a physical feature or portion thereof between these images; wherein the physical feature comprises shape, color, surface line, imprint, marking, deboss, emboss, groove or writing. Alternatively or in addition, the image processing step is carried out by detecting edges and lines in the at least one digital image and comparing said edges and lines with those in the reference image and determining if a match is found between said target medicine and the reference image for identifying the target medicine.

Alternatively or in addition, said image processing step further includes: adjusting said target medicine image based on skew or angle of said target medicine; scaling said target medicine image to match approximate size of said reference image; blurring said target medicine image; finding said target medicine image edges with an edge detector algorithm; finding said target medicine image lines with a line transform algorithm; marking said lines and edges into a modified target medicine image; overlaying said modified target medicine image over the reference image.

Alternatively or in addition, the method further includes the steps of: classifying said target medicine in an output category based on a successful or unsuccessful match with said reference image. Alternatively or in addition, the method further includes the steps of: utilizing a remote server and network connection to store said reference images. Alternatively or in addition, the method further includes the steps of: utilizing a remote server and network connection to store said reference medicine images and to carry out said image processing step.

Alternatively or in addition, determining if a match is found between said target medicine and said reference image further includes the steps of: using several matching algorithms in an iterative fashion to determine a match with highest probability or nonmatch with highest probability. Alternatively or in addition, said edges and lines with a reference image further includes: normalizing said match determination output; localizing regions of higher matching probability for identifying marks; recognize identifying marks using optical character recognition.

In another aspect, the subject technology relates to a medicine identifying device for identifying and sorting a target medicine from a mixture of medicines, including: an identification chamber by or within which a target medicine image is captured and thereafter processed for identification, wherein said identification chamber comprises an image capturing apparatus for creating at least one digital image of the target medicine; an image processing apparatus for comparing the at least one digital image with reference images and determining a match between the at least one digital image and a reference image for identifying the target medicine.

In a related embodiment, the device further includes a first queuing and/or sorting apparatus for queuing or sorting of the mixture of medicines before or during their introduction into the image capturing apparatus, and a second sorting apparatus for routing said target medicine to a desired location after the target medicine is processed or identified. Alternatively or in addition, said image processing apparatus includes a central processing unit, a main memory, and a storage unit; wherein the storage unit further comprises a database of the reference images comprising digital images of at least a portion of reference medicines.

Alternatively or in addition, the determining of a match between the at least one digital image and the reference images is based on a match probability output or percent identity between the at least one digital image and the reference images. Alternatively or in addition, the comparing of the at least one digital image with reference images includes comparing of at least one physical marker includes shape, color, surface line, imprint, marking, deboss, emboss, groove or writing or a portion thereof in the images. Alternatively or in addition, the device further includes: a network; a network interface unit; and a remote server for storing a database of reference images. Alternatively or in addition, the device is handheld. Alternatively or in addition, the device further includes a queuing apparatus for queuing medicines in a single file before they are introduced one-by-one to the identification unit.

Alternatively or in addition, said image capture apparatus comprises at least one digital camera having a lens, an aperture, a shutter, and an electronic image sensor. Alternatively or in addition, the device further includes a sorting apparatus for routing said target medicine from said identification unit to a desired location after the target medicine is processed or identified. Alternatively or in addition, said sorting apparatus further comprise flapper elements controlled by electric motors. Alternatively or in addition, said image identification unit further comprises a release controlled by an electric motor to keep the target medicine in the identification chamber longer for image processing and identification and to release said target medicine into the sorting apparatus once the image processing or identification is complete.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology. Like reference numbers indicate like elements. Furthermore, this specification is best understood when read in conjunction with the included figures, which disclose one or more exemplary embodiments of an image intensifier. In accordance with standard practices, various features are not drawn to scale and are used for illustration purposes only.

Figure 1:
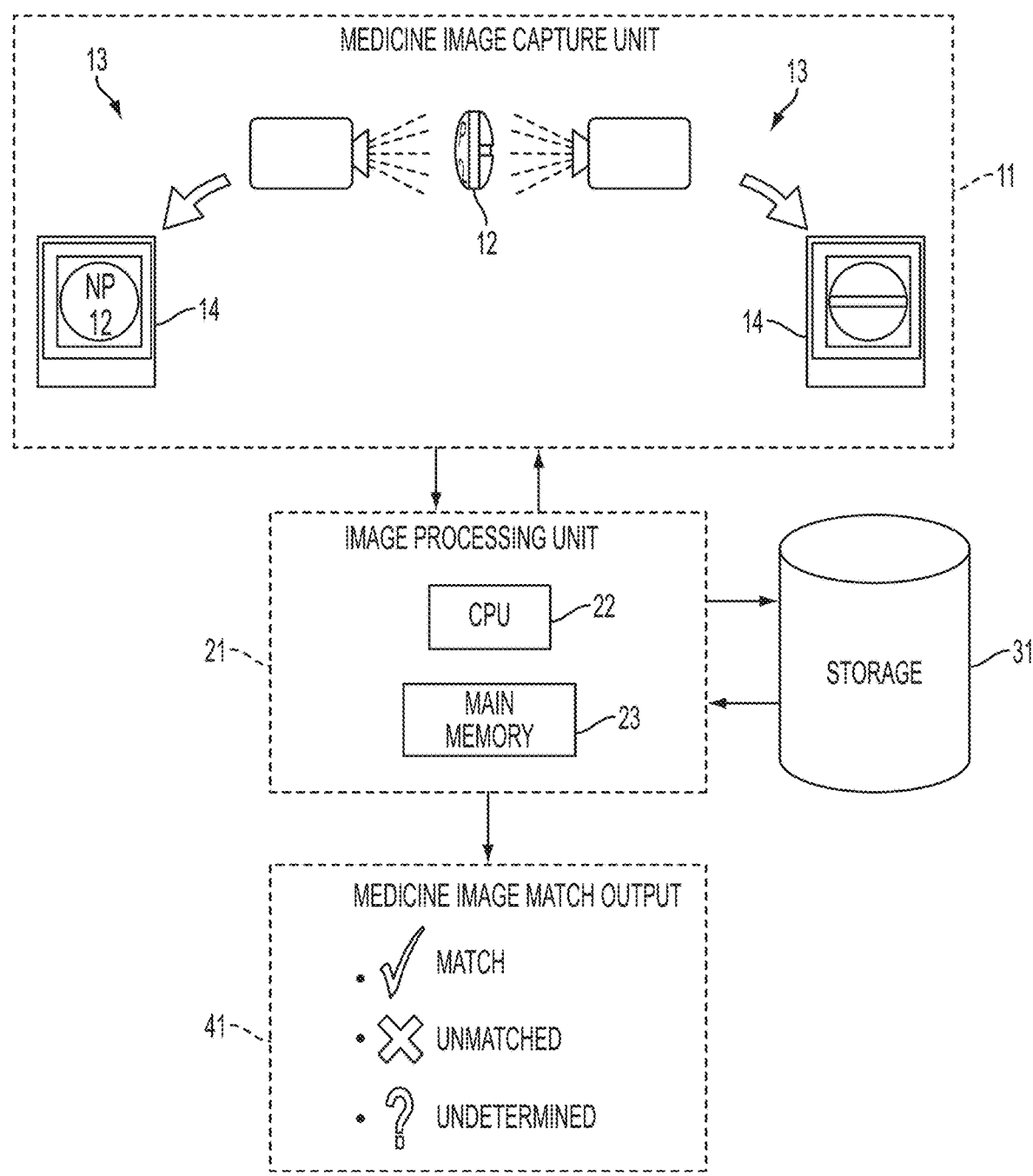
FIG. 1 shows a schematic diagram of an exemplary medicine identifying and/or sorting system of the subject technology.

It is to be understood that both the foregoing general description and the following detailed description are exemplary and explanatory and are intended to provide further explanation of the subject technology as claimed.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

To facilitate an understanding of the present subject technology, a number of terms and phrases are defined below:

Definitions

A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Underlined, bold and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Unless otherwise indicated, all numbers expressing quantities such as flow volume or flow rate and so forth as used in the specification and claims are to be understood as being modified in all instances by the term "about." The term "about" as used herein in reference to quantitative measurements not including the measurement of the mass of a compound, refers to the indicated value plus or minus 10%.

As used herein, the term "pill" refers to a wide variety of solid or semi-solid oral dosage forms used for delivering one or more compounds to a subject. The term "pill" includes, but is not limited to tablets of any shapes (e.g., round, oblong, oval, square, rectangle, diamond, 3-sided, 5-sided, 6-sided, 7-sided, 8-sided, heart shape, donut shape, or other shapes), capsules, caplets, gel caps, lozenges and the like.

Although the subject technology has been described with reference to pills, one of ordinary skill in the art recognizes that the method of the subject technology is not limited to sorting and identifying pills only. The method of the subject technology is equally applicable to sorting and identifying any pharmaceutical dosage form including medicines that are in liquid form and are bottled (e.g., syrups or ampules) or are for administration to an individual through routes other than an oral (e.g., suppositories). Therefore, as used herein the term "medicine" refers to any pharmaceutical dosage form that has at least one unique physical feature (e.g., shape, color, surface lines, imprints, markings, deboss, emboss, groove, writing, label, and other physical indicia) that can be used for identification and sorting by the system or device of the subject technology and in accordance to the method described herein. Thus, the term "medicine" includes any pharmaceutical dosage form that is identifiable by the method and device of the subject technology and includes, but is not limited to, tablets of any shapes (e.g., round, oblong, oval, square, rectangle, diamond, 3-sided, 5-sided, 6-sided, 7-sided, 8-sided, heart shape, donut shape, or other shapes), capsules, caplets, gel caps, lozenges, liquid medicines (in their original bottles), ampules, suppositories, inhalers and the like.

Reference is made herein to the attached drawings. Like reference numerals are used throughout the drawings to depict like or similar elements of the image processing medicine discriminator. For the purposes of presenting a brief and clear description of the subject technology, the preferred embodiment will be discussed as used for identifying and sorting medicines based on an image processing method and a system. The figures are intended for representative purposes only and should not be considered to be limiting (to e.g., pills) in any respect. For example, while the figures may show the device and system of the subject technology is configured to sort pills, the teachings of the subject technology is equally applicable to sorting other pharmaceutical dosage forms including liquid dosage forms (e.g., syrups, ampules) or aerosol dosage forms (e.g., inhalers), which are in their original bottles or containers.

The subject technology describes in terms of a method and system or device for analyzing a target medicine using an image capturing means and an image processing means, whereby the digital image(s) of a target medicine is taken or created by the image capturing device and, by the image processing device, said digital image is compared to reference medicine images stored within a database to determine the identity of the target medicine. The system is deployed within a medicine sorting device or via a handheld image capture and processing device. The medicine sorting embodiment of the system accepts several medicines and analyzes each separately, while providing output in the form of a sorting process or direct communication with the user. The handheld system employs a handheld electronic device (e.g. a smartphone device) that includes a camera of sufficient fidelity and a processing means for analyzing and comparing the target medicine image to reference images. The reference images are stored locally on the device within a storage means, or alternatively the reference images are stored on a remote server, whereby the handheld device or sorting embodiment has the capability of communicating with the remote server via a network interface means (e.g. a wireless antenna chip or Ethernet port). The method deployed for analyzing the medicines utilizes an image processing unit having several line and surface algorithms, whereby the details of the medicine surface characteristics and the shape or geometry of the medicine is compared to a plurality of reference medicine images within a retrievable database, whereby the success of the match is given probability as to an absolute match between the target medicine and a reference medicine image. The match probability using several different matching algorithms are compared with one another to determine the highest probability match before communicating to the user the identity of the medicine (if a match is indeed available in the reference medicine database and if the target medicine can indeed be analyzed given its surface properties). In some embodiments, the success of the match between the image of the target medicine and the images of the reference medicines is given as percent identity. For example, a percent identity of 70% or more indicates a match. In some embodiments a percent identity of 80% or more, 85% or more, 90% or more, 95% or more, or 98% or more, indicates a match between the target medicine and the reference medicine, which results in identification of the target medicine.

Referring now to FIG. 1, there is shown a schematic diagram of the elements of the present system, whereby the system is capable of analyzing a target medicine 12 based on an image processing method and comparing the processed image 14 to a stored database of known medicine images. The system comprises an image capture unit or apparatus 11, an image processing unit 21, and a storage means 31, whereby the elements function to provide an image processing computer system that provides a medicine match output 41 based on the results of the processing method. The image capturing means 11 preferably comprises at least one digital camera 13 or suitable image capturing technology that is capable of creating a digital image 14 of a target medicine 12 or a portion thereof, of sufficient fidelity such that the target medicine's surface characteristics such as imprints, lines, contours, colors, markings, geometry, and texture can be seen with clarity for further processing. The camera 13 further includes elements commonly found in the art of digital image capturing devices, including a lens, an aperture, a shutter, an electronic image sensor, and an illuminating flash. Multiple cameras 13 may be deployed to simultaneously capture an image 14 of various sides of the medicine for processing and surface recognition and for improved matching. In an embodiment, the camera(s) 13 are installed at various locations in the system of the subject technology and are capable of imaging a medicine as various locations and from different angles.

The image processing unit 21 comprises a processing means 22 such as a microprocessor or central processing unit (CPU) 22 and a main memory 23. The processing means 22 carries out programmed instructions of the matching method and carries out the operational instructions for the system elements. A storage means 31 stores digital information related to the reference images and the processing instructions for which the processing means 22 to carry out. A remote storage means 31 may also be utilized to retain the reference image information, thus reducing the local storage capacity requirements and allowing for updates to the database of images and the system to quickly be uploaded or changed without uploading new information to the local storage 31. The local storage means 31 comprises a mass storage device such as a computer hard disk or removable media, while the remote storage means may comprise a hard disk or server accessed remotely through a network accessed using a network interface means such as a wireless antenna chip or Ethernet port. In an embodiment, the storage means 31 is a cloud database. In another embodiment, the storage means 31 is a national or international medicine registry database containing detailed data about all physical and chemical attributes and characteristics of any and all medicines (including illicit drugs) produced anywhere in the world. The database further includes drug interaction data, poison control and prevention information, and any other information that may be of use to physicians, nurses, emergency responders, law enforcement officers, soldiers or anyone who may be interested learning about the identity or use of a medicine. This database or registry is continuously updated by information received from different agencies (e.g., Food and Drug Administration, Environmental Protection Agency, Drug Enforcement Agency, Customs and Border Protection Agency, and like agencies from around the world), hospitals, organizations and drug companies.

In operation, the image of a target medicine 12 is first captured using the image capture unit or apparatus 11, whereby at least a portion or one side of the medicine 12 is captured. Thereafter, the image processing unit or apparatus 21 interrogates the target image 14 and makes modifications thereto to highlight its shape, color, surface lines, imprints, markings, deboss, emboss, groove, and other physical indicia or characteristics. The processing means 21 then compares the target image 14 with reference images within the storage means 31 in an iterative process to determine an appropriate match. Several matching criteria are used, where after the medicine 12 is classified into, for example, one of three output categories 41: the target medicine decidedly matched with a referenced medicine image, the target medicine being unmatched, or the target medicine match being undetermined based on the quality of the target medicine, its captured image, or based on the limited extent of the reference image database. The output 41 is provided to a user in a plurality of ways, including a visual indication of the match output or by sorting the target medicine 12 based on a category (e.g., match/unmatched/undetermined). In case of a match, additional information may be displayed to the user. This information includes, for example, identity of the target medicine, the therapeutic category of the medicine, whether the medicine is a controlled substance or not, what should be done in case of overdose of the medicine, or various other information that may of use to the user. In an embodiment, the output 41 is linked to a sorting mechanism that will allow for the matched medicines to be routed to and sorted in specific bins or containers.

Figure 2:
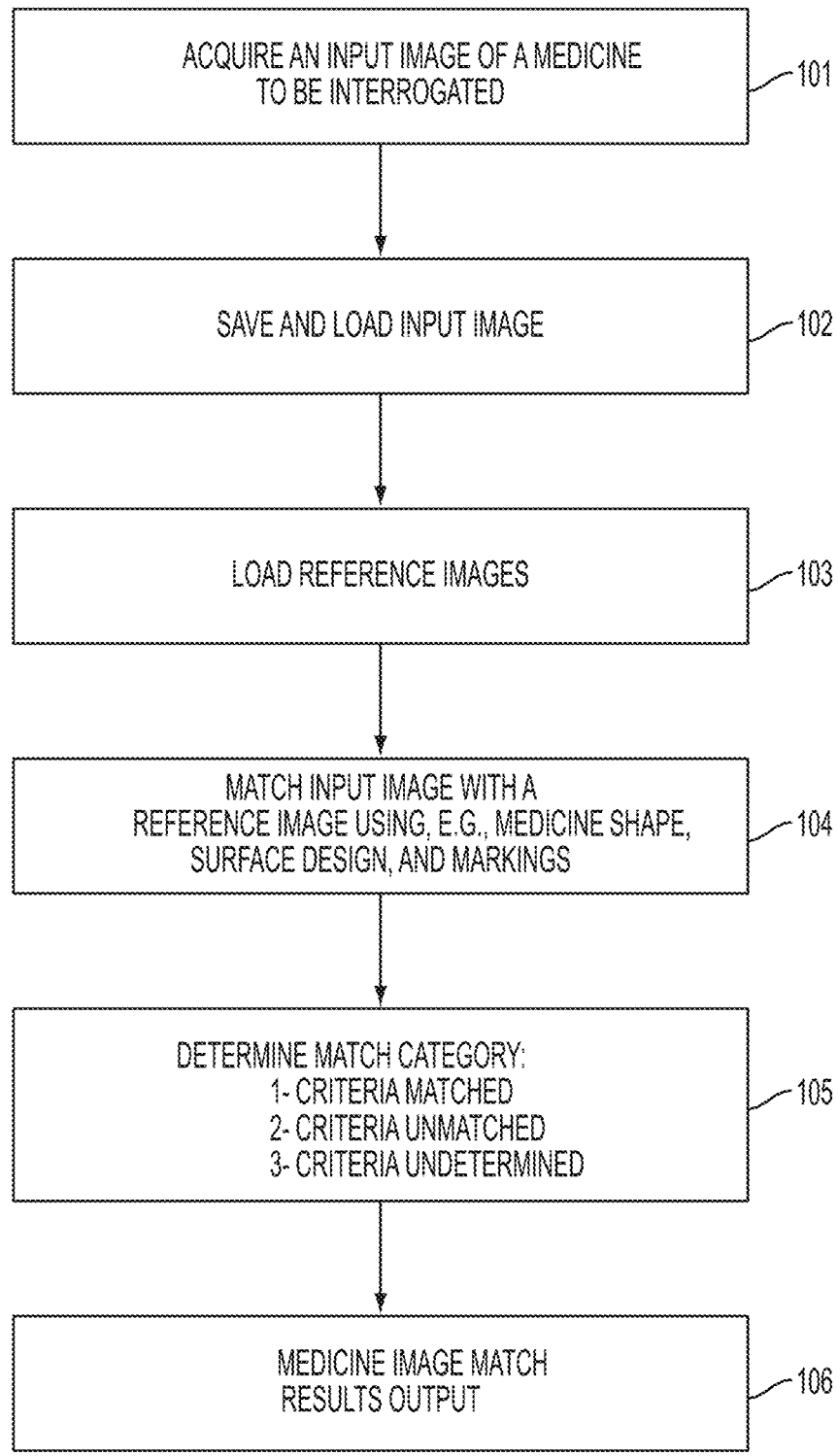
FIG. 2 shows a flow diagram highlighting the high level steps of the present method and system.

Referring now to FIG. 2, there is shown a flow diagram outlining an exemplary method for carrying out the image processing of the subject technology. According to this exemplary configuration, a target medicine is first interrogated for its features and then identified based on reference medicine images. The method initiates when a target medicine image, or a portion thereof, is acquired 101 by the image capture means such as a camera. This forms an input image to be analyzed, modified, and then compared with reference images in the system. The input image is saved 102 to the storage means and accessed using the main memory of the processing means. Thereafter, the main memory of the processing means loads consecutive references images 103 from the storage means to be compared separately with the target image. The target image is then analyzed using a matching algorithm and compared 104 with each reference image, loaded consecutively. The geometry of the medicine, the lines of the medicine surface, the grooves (if any) on the medicine, the color(s) of the medicine, or other physical attributes of the medicine are all compared against the loaded reference image to determine a probable match.

The matching process is an iterative process by which several different matching algorithms are deployed to determine the algorithm that provides the highest probability of match over a confidence interval. If a suitable match threshold is not surpassed, consecutive reference images are cycled to determine a more appropriate and higher probability match. If the highest match probability does not meet a suitable threshold, the output 105 is revealed as unmatched and the medicine identity is not claimed. If the matching probability is sufficiency low or if the processing means cannot find suitable features on the target medicine to match, the output 105 is shown as undetermined. Finally, if a suitable match is found, the medicine identity is revealed 106 to the user or used in the system to sort the medicine appropriately. This process utilizes the image processing means to cycle through matching algorithms and the reference images to match the target medicine with sufficient certainty. In an embodiment, the fidelity of the image capture means, therefore, the robustness of the image processing means, and the comprehensiveness of the reference image database are suitable to provide accurate output results, while also preventing false positives or false negatives.

Figure 3:
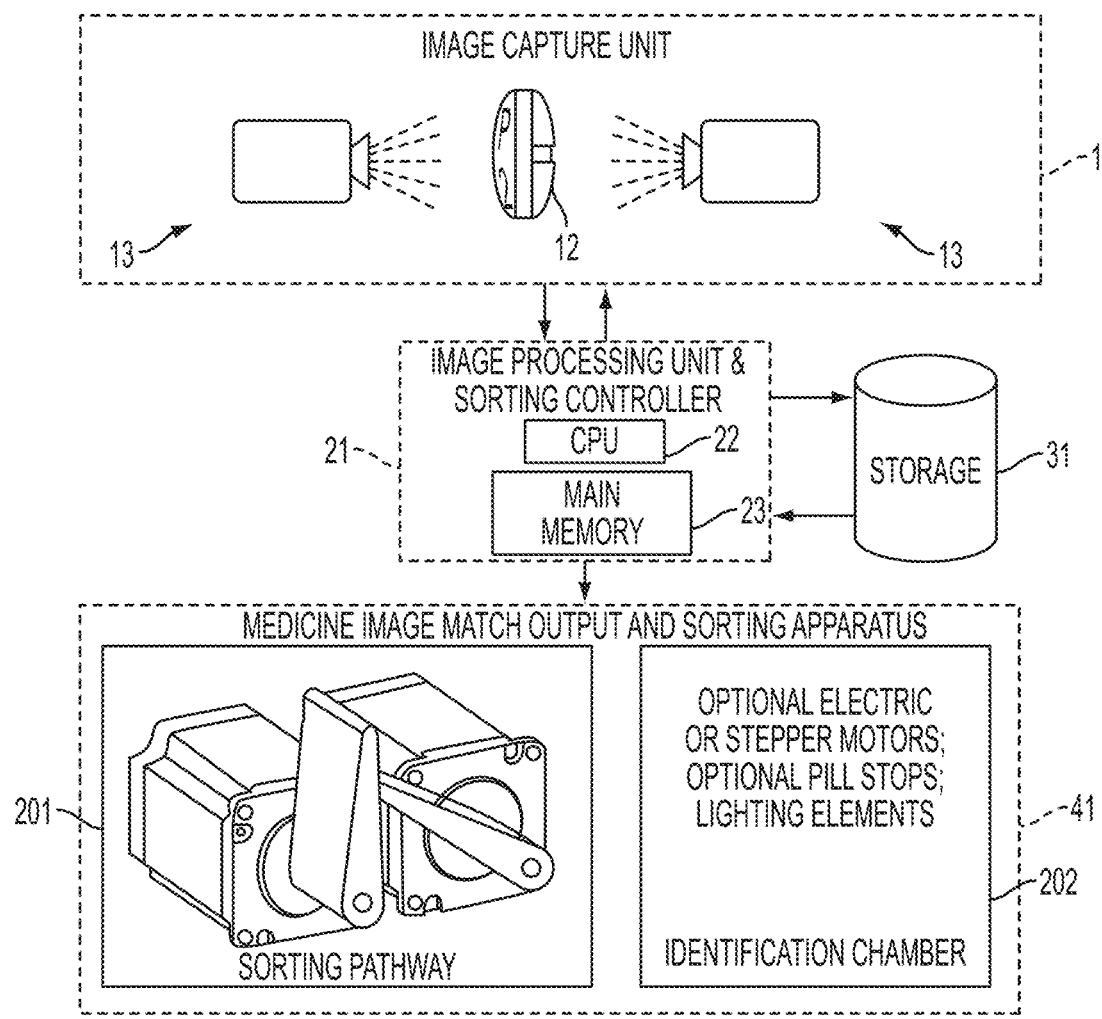
FIG. 3 shows an embodiment of the subject technology shown in a schematic diagram, whereby a sorting device operates based on input from the present system and method.

Referring now to FIG. 3, there is shown a schematic and exemplary view of the subject technology, wherein the elements of the medicine sorting embodiment are shown. The present method, when deployed in a medicine separating apparatus, employs the same aforementioned system elements, however the output 41 involves sorting the target medicine based on the results of the image processing and the matching results. In this embodiment, at least one camera 13 is present within the system to function as the image capture unit or apparatus 11. The image processing unit or apparatus 21 functions as a means to processing the target medicine image, the image capture unit controller, and the controller of the sorting apparatus 41 after the medicine match probability has been determined. The image processing unit or apparatus 21 comprises the processing means 22 and main memory 23, which draws instructions from a storage means 31 to process the captured image of the target medicine and to compare the captured image to reference images also stored on the storage means 31. As mentioned, the reference images may also be stored remotely on a secondary storage means to reduce local storage requirements and to improve efficiency of updating the system. Based on the results of the image processing, the match output 41 comprises releasing the target medicine from an identification chamber to a sorting pathway or chamber. The medicine travels to a sorting pathway and is routed to a specific bin or collection chamber. It is contemplated that electric motors or stepper motors may be utilized in the identification chamber to facilitate the identification the medicine (by slowing or stopping the medicine for imaging) and also to direct the medicine through a particular pathway 201 using flappers or other suitable structures. The exact design and structural elements deployed within the sorting device can vary depending on the desired application, desired output, and the user requirements; however the basic system elements are retained prior to the sorting process. In an embodiment, a medicine travels through a plurality of image processing units and/or sorting pathways to be finally sorted in a desired storage bin.

In an embodiment, to facilitate passage of the medicine 12 through the identification chamber 202, the chamber is free of electric or stepper motors designed to stop the medicines as their images are captured. Instead, in some embodiments, the chamber includes medicine stops. Medicine stops are obstructions within the identification chamber 202 that provide a means for slowing or temporarily stopping the medicine 12 as the medicines travels through the identification chamber 202. This will minimize any blurring of the medicine image. It will also allow for the system to have more time to identify the medicine as the medicine approaches or enters the medicine pathway to be routed to a specific bin or collection chamber.

A medicine stop may be an obstruction (e.g., one or more flaps, or the like) created that disrupts the natural traveling rate of the medicine 12 through the identification chamber 202. An obstruction may be any deviation from the smooth surface of the wall in the identification chamber 202. By way of example only, a flap, bump or the like may be placed within the identification chamber at or near the regions where the camera(s) 13 or imaging devices are installed. A medicine 12 traveling over the flap or bump will naturally slow down or stop for a fraction of second. In some embodiments, friction-creating protrusions, such as brushes, may project into the medicine path to slow down the rolling or falling medicine through the identification chamber 202. If the obstruction is placed within the identification chamber 202, the image capture device 13 can capture the image of the medicine as it slows down or stops, allowing for a clear shot. In embodiments utilizing friction creating obstructions, such as bumps, protrusions, brushes, and the like, the obstructions may be adjustable so that if the medicine is stopped, the obstruction can be moved out from the pathway of the medicine to allow the medicine to resume forward or downward towards the sorting pathway and collection bins.

In some embodiments, no obstructions or medicine stops are utilized. In other embodiments, the medicine may be transported through the image capturing device and image processing device by a conveyor belt. The imaging device(s) 13 may be high speed cameras that can capture a clear image of a moving medicine 12. Furthermore, the speed of the medicine 12 may be adjusted by adjusting the angle of the identification chamber relative to the ground to slow the medicine 12 down as necessary depending on the quality of the imaging device(s) 13.

In some embodiments, a trigger may be set up to time the image capturing process to acquire an image just as the medicine 12 passes in front of the image capturing device(s) 13. For example, a beam of light may be directed transversally through, or onto, the wall within the path of the medicine 12. When the medicine 12 passes through the beam of light to disrupt the transmission of the light, a signal can be sent to the camera(s) 13 to acquire the image immediately or within a specified time. A similar trigger can be set up for, or shared with, a second, third, fourth, and so on, camera(s) 13.

To assure the imaging device(s) 13 can capture the entire image or a large portion of the image of the medicine 12, the image field may be broad or that several imaging device (3) capture the target medicine image from different angles. In some embodiments, once the trigger is actuated, the imaging device(s) 13 can begin capturing a series of images in rapid succession for a period of time. Alternatively, a stop trigger can be positioned downstream of the image capture device such that actuation of the stop trigger stops the image capturing process. The stop trigger, like the acquisition trigger, may be a beam of light, disruption of which causes the image capture device to stop taking pictures. In another embodiment, the imaging device(s) 13 continuously acquire images.

In some embodiments, lighting can be installed within the identification chamber 202 at or near the imaging device(s) 13 for providing sufficient lighting for capturing better quality images of the target medicine 12. The lighting consists of a plurality of lighting elements affixed in and around the medicine pathway through the identification chamber 202, for example, in or around the flaps within the identification chamber 202, such that medicines in this region are illuminated.

The emission source for the lighting elements may be fluorescent, halogen, xenon gas, light emitting diode ("LED") or the like. In one embodiment, the lighting elements are high current, high intensity, flash-LEDs, due to their longevity, physically robust design, and low heat dissipation. The lighting elements may be affixed to the image identification chamber by solder, glue, epoxy, mechanical fasteners, or the like. The electrical leads of the lighting elements may be connected in series, parallel or some combination, to an external power source, and/or triggering source, via wires.

Figure 4:
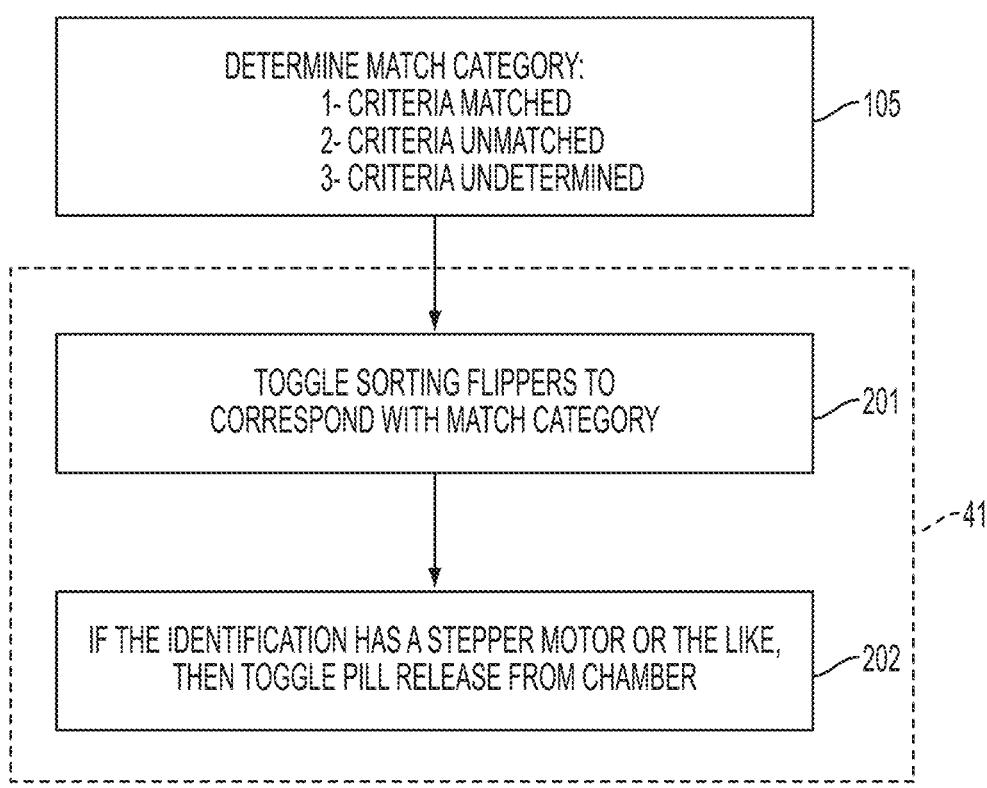
FIG. 4 shows the sorting device output steps based on the matching category provided by the system.

Referring now to FIG. 4, there is shown a flow diagram related to an exemplary embodiment of the output 41 of the medicine sorting embodiment of the present system. In this embodiment, after the target medicine match category 105 has been determined, the processing means communicates with the electric motor controllers or stepper motor controllers to toggle at least one sorting means 201 within the device to direct the target medicine to a specific location based on its match category 105. In one embodiment, flappers are utilized to direct the target medicine from its identification chamber and into a prescribed bin. In an embodiment where the target medicine is first supported within the identification chamber, once the match category 105 has been determined and the flappers have been toggled 201 to the correct output bin, a release within the target medicine identification chamber 202 is toggled to drop or flow the target medicine to the output bin. This notifies the user whether the medicine is matched, or within what category the specific medicine can be classified. In other embodiments, a visual output may also accompany the physical sorting process such that the user is notified of the medicine match category and/or information about the medicine. In another embodiment, the user selects where or which bin a medicine of a specific characteristic (e.g., pain killers, antibiotics) is to be sorted in.

Figure 5:
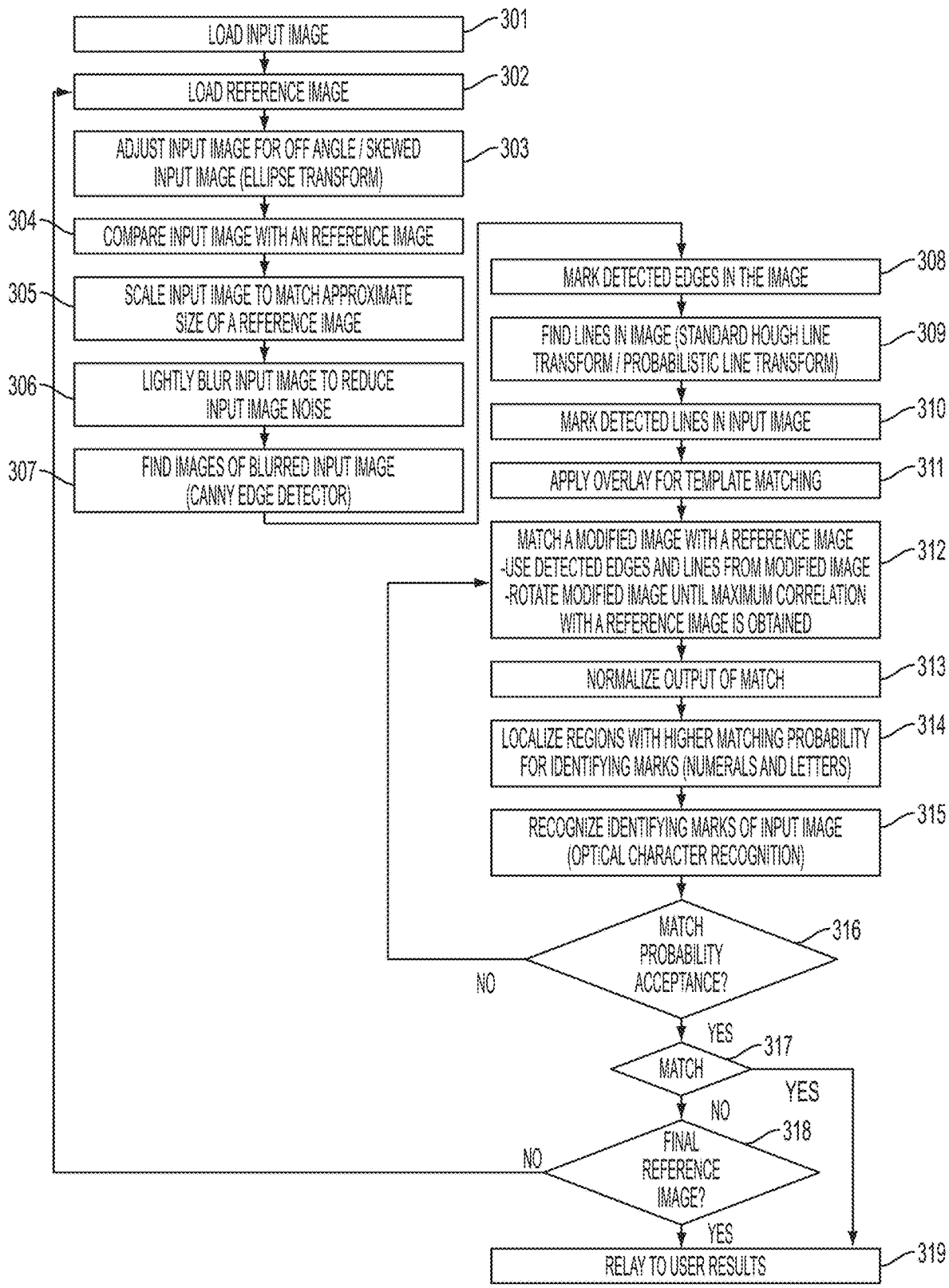
FIG. 5 shows a flow diagram of the present medicine matching method.

Referring now to FIG. 5, there is shown a flow diagram outlining an exemplary medicine image processing method according to the subject technology. The first step in the process involves dropping or sending a target medicine through an identification chamber or isolating an individual medicine therein to be processed, after which at least one image of the medicine is captured. The target medicine image forms an input image for the process that is first loaded 301. While the target medicine image is loaded, the first reference medicine image is loaded 302 from within the reference image database. From here, the input image is adjusted 303 to account for an image of the medicine that is not perfectly parallel to the image capture unit lens. Depending on the circumstances with which the input image is taken, the medicine can be tilted and thus skew the image thereof, creating an illusion of a deformed or skewed medicine shape and corresponding surface lines. To compensate for a skewed input image, the method performs an ellipse transform operation to project the skewed image onto a plane whose normal is directed at the camera lens. Adjusting the input image for off-vertical camera angles involves recognizing the boundary of the object and if the boundary has an elliptical shape rather than a circular shape. The major and minor axes are then determined; whereafter the transformation proceeds by determining the major and minor axes of the target medicine and stretching the image parallel to the minor axis while shrinking it parallel to the major axis until they are equal. This may also require some keystoning operations. The goal is to provide a corrected input image for proper comparison with reference images.

Once the input image has been transformed 303, the input image is compared 304 with the loaded reference image. The input image is scaled 305 uniformly to match the approximate size (diameter) of the reference medicine image. To reduce noise and minor imperfections of the target medicine surface (and background area) within the input image, the input image is blurred 306 to soften the image for improved detection of its major surface lines and edges. Once blurred, the edges on the input image are detected 307 using a Canny edge detector operation. Major edges on the target medicine are thus detected and thereafter marked 308 on the input image for comparison to the reference image. After edges are detected, surface lines of the input image are detected using a line transform operation (Standard Hough Line Transform or Probabilistic Line Transform). These lines are also marked on the input image 310, modifying the input image based first on detected edges and then based on detected lines. The input image is modified and stored within the storage means. Once edges and lines are marked on the input image, the input image is overlaid onto the reference image 311 for the matching procedure to commence. Up to this step, the steps have involved modifying the input image such that the matching steps will proceed with greater probability of match if indeed a match does exist within the reference image database.

Matching the modified input image with the loaded reference image proceeds by using the detected edges and lines from the modified input image, rotating the modified input image, and sliding the modified input image to correspond with the lines and edges of the reference image. Either the reference image or the modified input image may be rotated and slid during this comparison. The image being rotated and slid is moved one pixel at time. At each pixel location, a metric is calculated that represents how "good" or "bad" the match is at that pixel location (or how similar the reference is to that particular area of the modified input image). By rotating, the image being handled is rotated in a sequence of five degrees from center, and repeating the sliding process. This rotation can be repeated for a full rotation (360 degrees) of the image being handled (the modified input image or the reference image). For each pixel location during the rotation and sliding operation, the metric is stored in a results matrix (R). Each location (x,y) in R contains the match metric.

The process of matching the modified input image with the loaded reference image 312 proceeds using several different algorithms to determine the highest match probability. The highest match probability is then utilized as the result of the matching operation 312. These percentages can change dynamically because of the lighting on the target medicine surfaces and the wear of the medicine. The following is a list of algorithms utilized in the matching procedure. Each matching algorithm is well known in the art of image processing. The matching process proceeds by finding areas of an input image matching the template image whereby an each of the following algorithms is utilized:

Squared Difference Algorithm$^2$:

$$R(x, y) = \sum_{x',y'} (T(x', y') - I(x+x', y+y'))^2$$

Normalized Squared Difference Algorithm:

$$R(x, y) = \frac{\sum_{x',y'} (T(x', y') - I(x+x', y+y'))^2}{\sqrt{\sum_{x',y'} T(x', y')^2 \cdot \sum_{x',y'} I(x+x', y+y')^2}}$$

Cross Correlation Algorithm:

$$R(x, y) = \sum_{x',y'} (T(x', y') \cdot I(x+x', y+y'))$$

Normalized Cross Correlation Algorithm:

$$R(x, y) = \frac{\sum_{x',y'} (T(x', y') \cdot I(x+x', y+y'))}{\sqrt{\sum_{x',y'} T(x', y')^2 \cdot \sum_{x',y'} I(x+x', y+y')^2}}$$

Correlation Coefficient Algorithm:

$$R(x, y) = \sum_{x', y'} (T(x', y') \cdot I(x + x', y + y'))$$

where:

$$T(x', y') = T(x', y') - 1/(w \cdot h) \cdot \sum_{x'', y''} T(x'', y'')$$

$$T(x + x', y + y') = I(x + x', y + y') - 1/(w \cdot h) \cdot \sum_{x'', y''} I(x + x'', y + y'')$$

Normalized Correlation Coefficient Algorithm:

$$R(x, y) = \frac{\sum_{x', y'} (T(x', y') \cdot I(x + x', y + y'))}{\sqrt{\sum_{x', y'} T(x', y')^2 \cdot \sum_{x', y'} I(x + x', y + y')^2}}$$

The foregoing algorithms are utilized to match the modified input image to the reference image once overlaid over one another. All of these algorithms can be cycled through individually or some combination thereof. The highest match probability resulting from the deployed algorithms are then utilized as the match result for output of the system.

Figure 6:
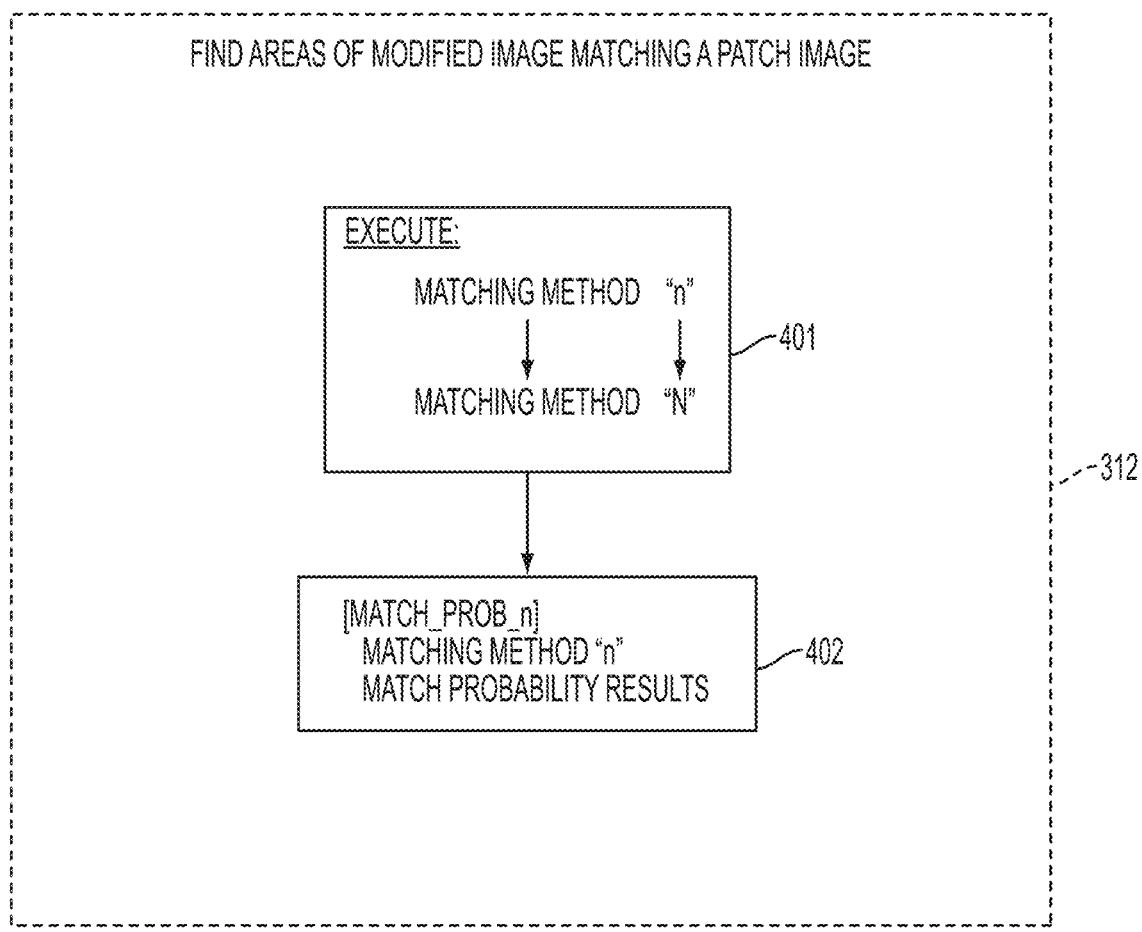
FIG. 6 shows the algorithm used to develop a strong match between a target medicine being analyzed and a reference medicine image.

Referring now to FIG. 6, there is shown an exemplary expanded flow diagram of the matching procedure 312, whereby the matching methods n through N are executed 401 in an iterative process. The given matching algorithm derives a match probability 402, which is then utilized in the overall flow of FIG. 5 to compare to the algorithm's match probably against preceding match probabilities to determine which algorithm has provided the highest match probability. Referring back to FIG. 5, the match output from the given algorithm is normalized 313 before regions of the input image with higher matching probability are identified 314 for matching surface marks and indicia of the medicine. The identifying marks or indicia are then recognized 315 using, for example, optical character recognition (OCR) to determine what the indicia read. Once the matching procedure is conducted, the probably of the match is then compared against any previous algorithm's probability to determine if the probably of the given iteration is acceptable 316. If the matching algorithms have not been exhausted and if the matching probably is not to a sufficient standard, the matching process 312 initiates again with a different matching algorithm, whereby its match probability is determined. This proceeds until a sufficiently high probably of match is determined or if the algorithms have been exhausted.

If the results indeed provide a match with a sufficient probability, the results of the match being relayed 319 to the user or utilized in the sorting process. If the match probability is not sufficiently high, a subsequent reference image is loaded 302 for matching another reference medicine to the input image. If the reference images within the database have been exhausted, the results of the non-match are relayed to the user 319 or forwarded to the sorting process for appropriate action. In this way, the input image is matched using several different matching methods for each reference image until a satisfactory output is reached. This is a sample flow that fulfills the goals of the present image processing method. It is contemplated that departures or more efficient steps may be incorporated in later designs of the method, however the basis of the medicine identification procedure is image processing using line and edge detection and probabilistic matching algorithms that scan each pixel of the input image against the reference image and identify physical characteristics or indicia on the target medicine surface.

In some embodiments, to provide for efficiency in the comparison process, indexed lists of image identifiers (such as characterizations based upon the color content or edge content of partitions of an image) are maintained, and the count of similar characterizations of an image is determined by the count of occurrences of the image's identifier in selected lists. The selected lists are determined by a characterization of a target image from which similar images are to be identified. For example, the indexing and retrieval techniques disclosed in U.S. Pat. No. 6,253,201 (hereby incorporated herein by reference) are suitable for use in the subject technology. The indexing method allows for quick image retrieval and comparison, which leads to a faster or real time identification of the medicines as they travel through the identification chamber 202. Multiple indexes can be associated with one or more characteristic measures of each partition, allowing for image retrieval based on one or more characteristics of the target image.

Figure 7:
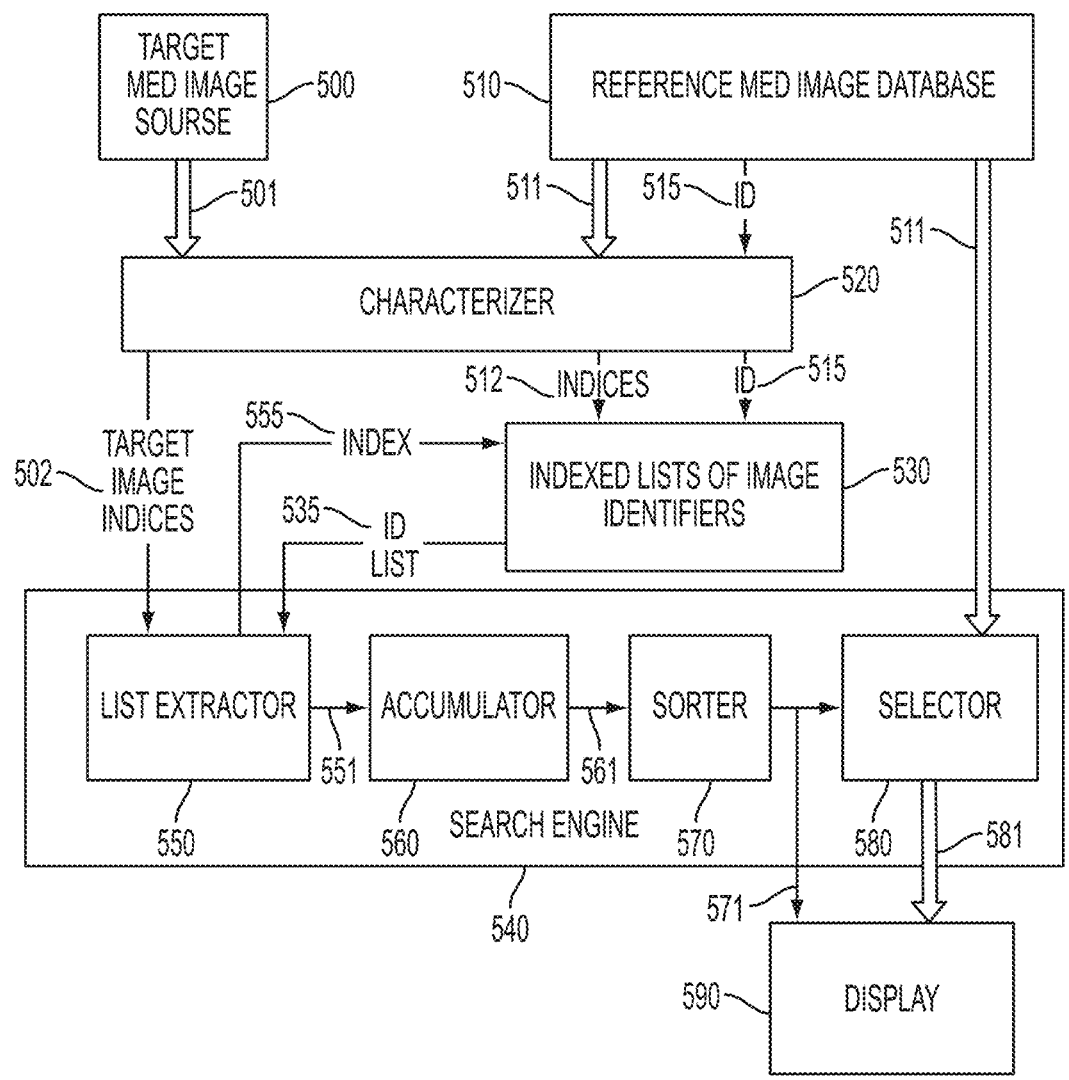
FIG. 7 illustrates an example block diagram of an image retrieval system in accordance an exemplary embodiment of the subject technology.

FIG. 7 illustrates an example block diagram of an exemplary indexing and image retrieval system. The image retrieval system includes a characterizer 520 that produces indexes 502, 512 to lists of image identifiers 530, and a search engine 540 that processes selected lists of image identifiers 535 to determine the images 581 that have a high number of occurrences 561 in the selected lists 535.

By introducing a medicine to the medicine identification system of the subject technology, a target medicine image 501 is provided to the image retrieval system of FIG. 7 to determine the reference medicine images 511 of a reference medicine image database 510 that are similar in characteristics to the target medicine image 501. The source 500 of the target medicine image 501 may be a digitizer, a camera, and the like.

The reference database of images 510, which is similar to the reference image storage database 31 shown in previous figures, may be located in a local or remote disk storage, a memory device, a central server, an online server, a cloud computing site, and the like. The reference medicine images are created and stored using input devices such as scanners, digitizers, and cameras, as discussed above. Additionally, they could be a series of related images as might be found in an MPEG encoded video, or a conventional video program. The term database in this context means a collection of items (images), each of which can be uniquely identified. As is known in the art, a database may be distributed, and need not reside in a single physical device, nor need the addressing scheme be common among all devices. That is, as used herein, the reference medicine image database 510 is independent of the physical media that contains the images, and independent of the media dependent techniques for accessing each image. Each image 511 in the reference medicine image database 510 is provided to the characterizer 520 to create the indexed lists of image identifiers 530.

Figure 8:
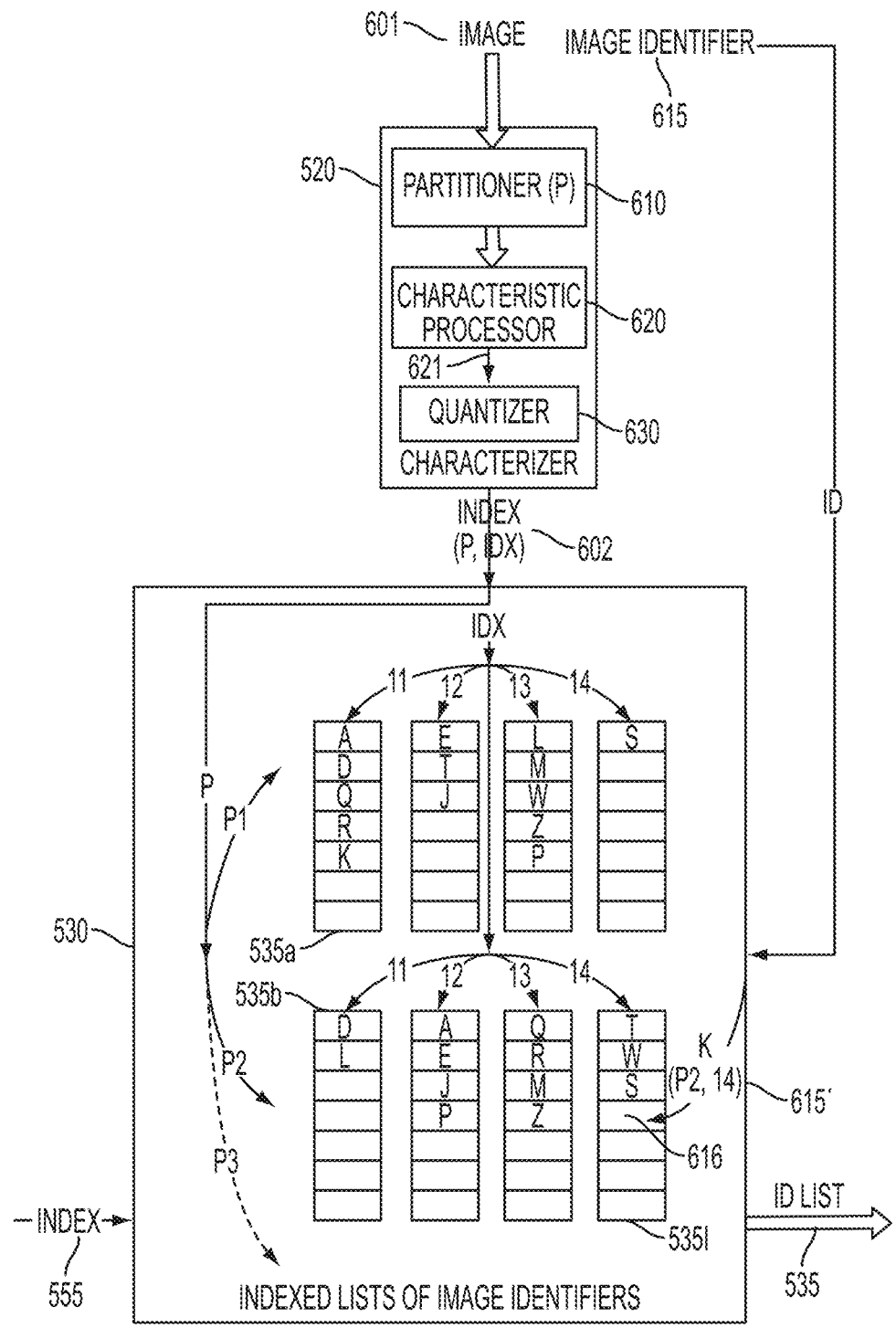
FIG. 8 illustrates an example block diagram of a characterizer that provides an index to indexed lists of image identifiers in accordance with an exemplary embodiment of the subject technology.

FIG. 8 illustrates an exemplary block diagram of a characterizer 520 that provides an index 602 to the indexed lists of image identifiers 530. The characterizer 520 includes a partitioner 610, a characteristic processor 620, and a quantizer 630. The partitioner 610 partitions an image 601 into an array of partitions; typically the array is a 4×4, 8×8, or 16×16 partitioning of the image. The index 602 includes an identification P of each partition, and an indexed characterization Idx that characterizes the partition as one of a set of predefined indexed characterizations. The characteristic processor 620 processes each partition P based on the characteristic used to describe an image and produces a characteristic measure 621 that describes the partition. In general, the characteristic measure 621 is a histogram of the occurrences of the components of the descriptive characteristic, for example, the number of occurrences of particular colors, or the number of occurrences of particular types of edges. Other techniques are known in the art for deriving a characteristic measure or set of measures that describe an image, such as combinations of particular shapes, etc. The quantizer 630 transforms the characteristic measure 621 that is produced by the characteristic processor 620 into one of a plurality of predefined indexed characterizations Idx. In the most straightforward example, the quantizer 630 transforms a histogram of occurrences of the components of the descriptive characteristic into a set of proportions of each component contained in each partition, and then quantizes each proportion into predefined 'bins' such as quartiles, octiles, etc. In the general case, each of the predefined indexed characterizations Idx is associated with a location in the parameter space of the characteristic measure 621, and a region about this location. The quantizer 630 determines the predefined indexed characterization Idx based on the region in which the characteristic measure 621 lies. The quantization provided by the quantizer 630 need not be uniform. For example, more indexed characterizations may be located in the area of the parameter space that corresponds to frequently occurring values of the characteristic measure, thereby providing for a greater degree of distinction among such values as compared to a uniform distribution of the indexed characterizations about the parameter space. The locations of the indexed characterizations are typically called the quantization levels, or quantization centers; for example, in a color characterization, the colors at the location of the indexed characterizations are termed the color centers. The quantization need not be un-valued. For example, multiple indexed characterizations may be provided for each characteristic measure 621, as will be discussed below.

Each index 602 provided by the characterizer 520 is used to store an identifier 615 corresponding to the image 601. Typically, the identifier 615 is a unique numerical value for each image 601, and this numerical value corresponds to a list of locations (not shown) that identify where the image 601 is located. For example, the location specified in the list corresponding to the identifier 615 may be a conventional computer path name that identifies a file that contains the image 601. Alternatively, the location could be text that is imprinted on a medicine, followed by the shape of the medicine. In FIG. 8, uppercase letters are used to represent the particular image identifiers 615.

The identifier 615 of the image 601 is stored in each list 535 that is associated with a partition P of the image that has an indexed characterization Idx. That is, for example, if partition P1 corresponds to the upper left corner of the images, and index I1 corresponds to an occurrence of predominantly red and blue colors, then the list 535a will be a list of the identifiers (A, D, Q, R, K) of all the images 511 in the database 510 that have predominantly red and blue colors in their upper left corner. List 535b corresponds to the images 511 in the database 510 that have predominantly red and blue colors in the area of partition P2, which may be, for example, the lower left corner of the images.

Multiple indexed characterizations may be provided for each partition. For example, characterization 14 could correspond to the occurrence of predominantly horizontal edges, or to a partition having an average brightness of 25 lumens, etc. In this manner, multiple characterizations of each partition (color, edges, markings, debosses, grooves, luminance, etc.) of a target medicine image 501 can be used to place the image identifier 615 into multiple lists 535. The retrieval of images can thereby include retrievals based on the similarity of images 511 to one or more particular characteristics of the target medicine image 501. The multiple characterizations may be of differing characteristics, such as color and shape, or of the same characterization, for example, a characterization of occurrences or intensities of each primary color. By providing multiple indexes of the same characterization allows, for example, a search for images having red colors in their upper right partitions, independent of the other colors that may also be present in the upper right partitions. Multiple indexes of different characterizations allow, for example, a search for images having horizontal edges and green color in the upper right partitions.

Figure 9:
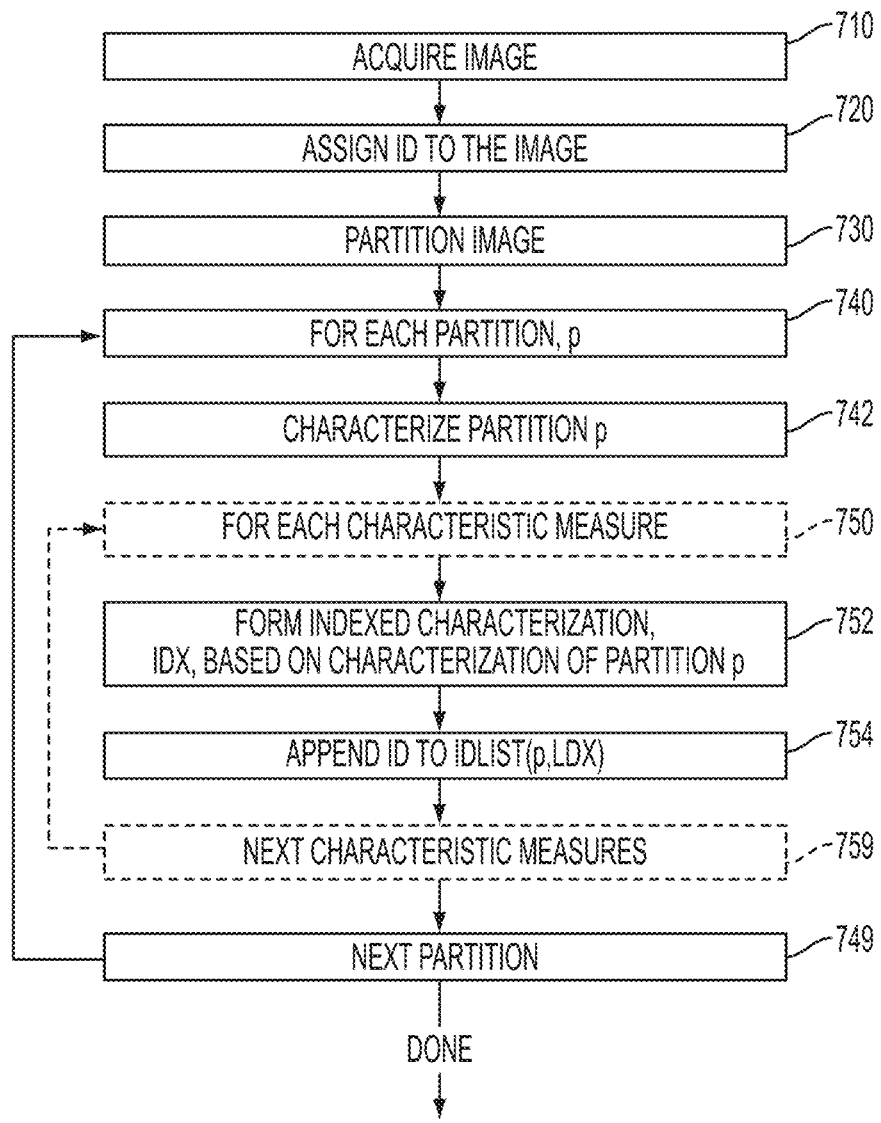
FIG. 9 illustrates an example flow chart for characterizing an image for entry in indexed lists of image identifiers in accordance with an exemplary embodiment of the subject technology.

FIG. 9 illustrates an exemplary flow chart for characterizing an image for entry in indexed lists of image identifiers. The medicine image, or a portion thereof, is acquired, in 710, and an image identifier ID is assigned, at 720. The image is partitioned, at 730, and each partition is processed in the loop 740-749. The partition is characterized at 742 to form one or more characteristic measures. Each characteristic measure, such as color or shape, is processed in the loop 750-759. At 752, the indexed characterization corresponding to the determined value of the characteristic measure at the partition is determined. The image identifier corresponding to the image is appended to the list of image identifiers having the same indexed characterization at the same partition, at 754. Each characteristic measure for each partition of the image is similarly processed, as indicated by the "next" blocks 759, 749. Note that the flowchart of FIG. 9 may be applied independently for each image that is being characterized for entry into the indexed lists of image identifiers 530. The only dependency is the availability of space in the indexed lists to append the image identifier ID. Techniques common in the art, such as dynamic linked lists, are used in the preferred embodiment to maximize the likelihood of the space being available to append the entry.

Figure 10:
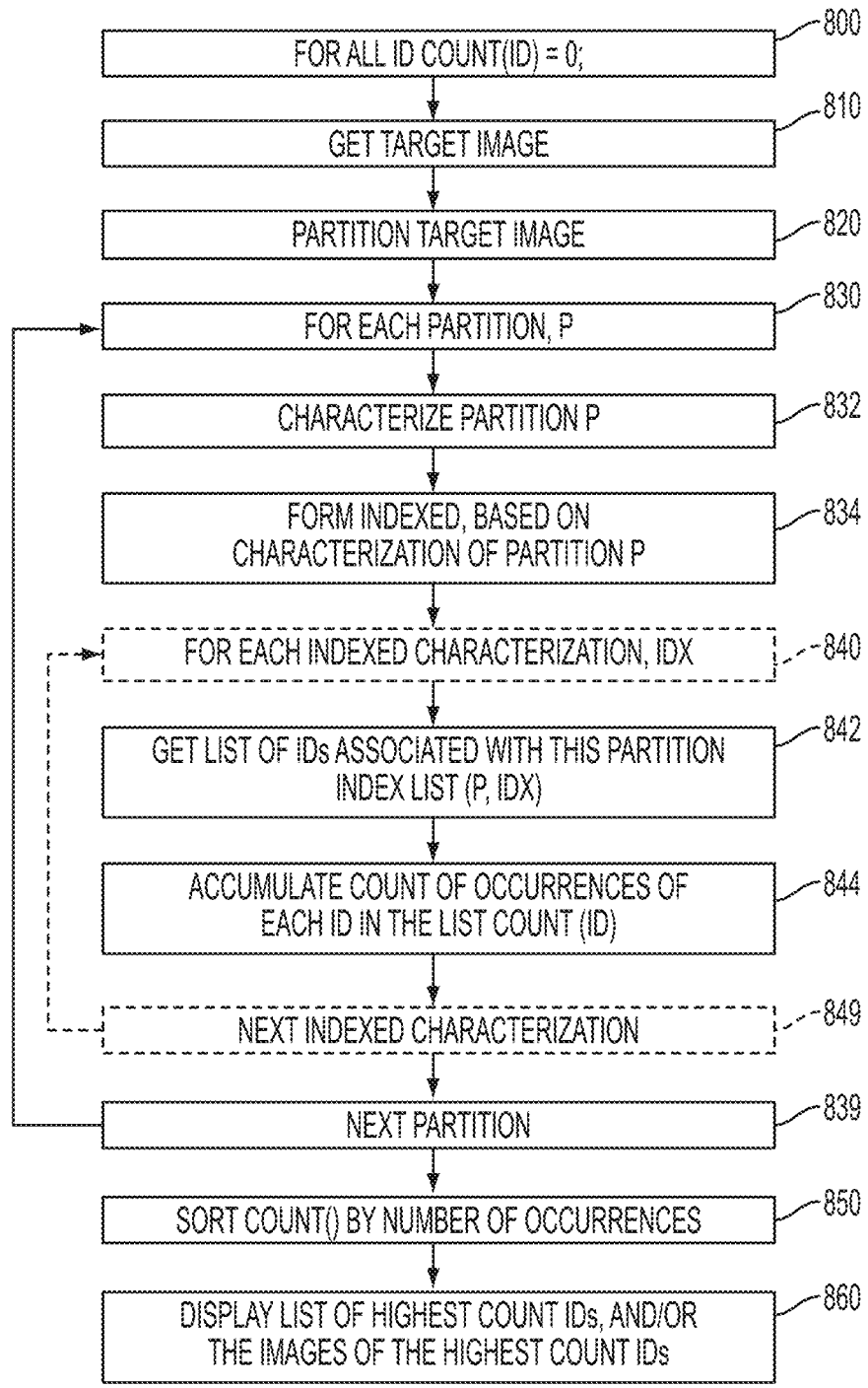
FIG. 10 illustrates an example flow chart for retrieving images that are similar to a target image in accordance with an exemplary embodiment of the subject technology.

FIG. 10 illustrates an example flow chart for retrieving characterized reference medicine images 511 that are similar to a target image 501. The similarity is determined by counting the number of occurrences of each reference image 511 that has a corresponding partition with the same characteristics as the target image 501. At 800, the count of the number of occurrences of each image identifier ID is initialized to zero. The target medicine image 501 is obtained and partitioned, at 810-820. Each partition of the target image is processed in the loop 830-839. The partition p is characterized at 832, using the same characterization measures as had been used to characterize the reference images 511, or a subset of these characterization measures. That is, for example, if the reference images 511 have been characterized by color and edge characteristics, the target image 501 may be characterized at 832 for color characteristics only, or edge characteristics only, or both color and edge characteristics. In this manner, for example, color target medicine photos can be compared for both composition and color. At 834, an indexed characterization Idx is determined for each characteristic measure, using the same quantization scheme used for determining the indexed characterizations of the reference images.

In an embodiment, multiple indexed characterizations Idx may be determined for each characteristic measure, to overcome quantization anomalies. Quantization anomalies occur, for example, when two images have similar characteristic measure, but receive differing indexed characterizations because the characteristic measures lie near the boundary between two indexed characterizations and the measure of each of the images lie on opposite sides of the boundary. At 834, multiple indexed characterizations are produced whenever the characteristic measure lies within a specified range of the boundary between indexed characterizations. Other algorithms for generating multiple indexed characterizations from a target characteristic measure, for example, associating overlapping quantization regions to each indexed characterization, may also be used.

Each indexed characterization Idx is processed in the loop 840-849. For each indexed characterization Idx of each partition P, the list of image identifiers associated with this partition index (P, Idx) is extracted from the indexed lists of image identifiers, at 842. As noted above, the list of image identifiers at each index is a list of all the images in the database 510 that have the same indexed characterization of the partition. At 844, the count of each image identifier ID that is contained in the extracted list corresponding to (P, Idx) is accumulated. If multiple indexed characterizations are associated with each partition P, this accumulation of counts is dependent upon whether the multiple characterizations are dependent or independent. For example, if the characterizations are independent, such as color and edge characteristics, an image identifier ID occurring in each of two lists (P, color-Idx) and (P, edge-Idx) accumulates two counts, thereby accumulating a higher count than an image identifier that only occurs in one of these lists. If the characterizations are dependent, however, such as redundant quantizations used to avoid quantization anomalies, as discussed above, an image identifier ID that occurs in multiple dependent-index lists accumulates a single count. The occurrence of an image identifier ID two dependent-index lists accumulates the same count regardless of whether it occurs in either or both of these dependent-index lists. In effect, the set of image identifiers associated with each partition is the union of the sets of image identifiers in each of the dependent-index lists associated with the partition. After all partitions are processed via the loop 830-839, the count variable that is associated with each image identifier contains the number of times each image identifier occurred in the lists that correspond to the indexed characterization of the partitions of the target image. That is, the count is correlated to the number of similar characteristics between the reference and target images.

At 850, the counts of the image identifiers are sorted, and the location of those having the highest count, i.e. those having the highest similarity to the target image, are presented to the user, at 860. In a preferred embodiment, the images corresponding to the image identifiers are presented to the user as well. Thus, as can be seen, the subject technology provides for a determination of those reference medicine images in a database 510 that have the most similar characteristics to the target medicine image 501, without requiring a direct comparison of the characteristics of the target image to each reference image.

Various other image retrieval and processing methods that can be used in the system or method of the subject technology are disclosed in, for example, U.S. Pat. Nos. 8,542,951; 8,503,777; 8,463,045; 7,840,081; 7,602,976; and 7,369,685, which are hereby incorporated herein by reference.

In another embodiment, a classifier may be used to classify the query image into one of a plurality of classes based on the representation of the query image. The classifier may include a neural network, a Bayesian belief network, support vector machines (SVMs), fuzzy logic, Hidden Markov Model (HMM), or any combination thereof, etc. The classifier may be trained on a subset of the representations of the images stored in the image database.

Referring now to FIG. 11, there is shown an exemplary cross section view of the medicine identification and sorting embodiment of the present disclosure. In this embodiment, the system utilizes a sorting means as an output based on the input image processing. In an embodiment, one or more imaging device(s) or camera(s) 13 are positioned along various sides of a medicine identification chamber 202 through which the target medicine travels (by e.g., gravity or by a conveyor belt) during image capture and processing. The medicine identification chamber 202 accepts a single medicine at a time, whereby medicines can be dropped into a medicine deposit area 902 having sloping sidewalls 903 or a funnel shape to direct a target medicine into the identification chamber for processing. In an embodiment, the target medicines are transported into the identification chamber in a single file or one-by-one by gravity or by a conveyor belt. In an embodiment, the target medicine may be supported within the chamber 202 via a perch controlled by the chamber release motor (not shown), which rotates the perch from a closed to and open position. When closed, a target medicine is supported on its edge for image capture of its different sides. When open, the perch withdraws from the interior of the chamber to allow the target medicine to drop into a sorting area. As provided above, the identification chamber may be free of electric or stepper motors designed to stop the medicines as their images are captured. Instead, in some embodiments, the chamber includes medicines stops. Thus, in another embodiment, the target medicine may be slowed down as it travels through the identification chamber by the medicine stops 906. Medicine stops are obstructions within the identification chamber 202 that provide a means for slowing or temporarily stopping the medicine 12 when it enters the imaging region(s) of the identification chamber 202. The medicine stop may be an obstruction (e.g., one or more flaps, or the like) created that disrupts the natural traveling rate of the medicine 12 through the identification chamber 202. In an embodiment, the entire or partial structure of the identification chamber 202 is made of transparent plastic or thermoplastic such as Plexiglas® or Lexan®. In another embodiment, the transparent surface in the identification chamber 202 is constructed of scratch resistant, optical grade glass such as Corning® Gorilla® Glass.

Figure 11A:
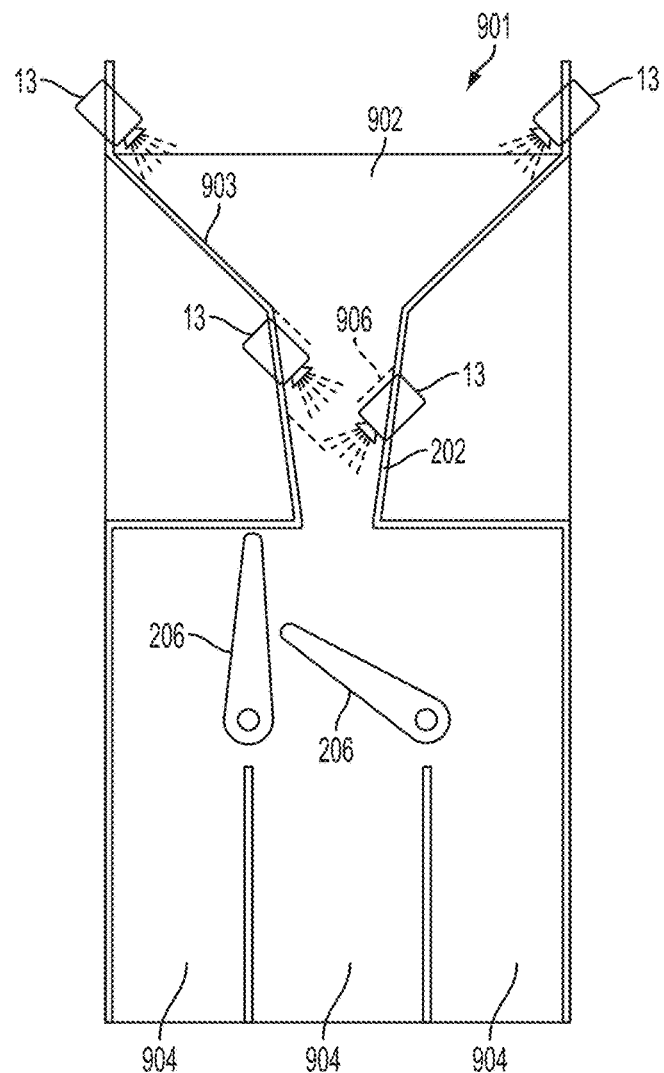
FIG. 11A shows a view of an exemplary embodiment of the subject technology deployed in a sorting device, whereby a plurality of medicines can be loaded and individually analyzed and thereafter sorted.

Once the target medicine is identified, the medicine continues its travel towards the sorting area where it will be distributed to collection bin by a distribution mechanism. For example, as shown in FIG. 11A, the flapper elements 206 within the sorting area control the direction of the target medicine after it has been identified, whereby the medicine is routed to a desired collection bin 904 therebelow. It is contemplated that the number of flapper elements 206 and design of the sorting area may take several different forms, depending on the needs of the user and the number of output categories desired. See for example FIG. 11B, where a linear distribution manifold is illustrated. The linear distribution manifold has an inlet 930 and a plurality of outlets 933*a-e* which are disposed above collection bins or another distribution mechanism. The manifold contains a chute 931 pivotally attached to a housing 932 of the manifold. The chute pivots so that a medicine entering the chute at the first end 930 can be directed to any one of the outlets 933*a-e*.

It is desired to show a functional embodiment that can be used to analyze and optically analyze medicines deposited into the device quickly and efficiently. The target medicines are placed within the deposit area 902 one by one, or alternatively a sorting or queuing means which can accept a plurality of medicines at once and convey them individually into the identification chamber. This sorting or queuing means will be discussed in more details below, whereafter the medicines are sorted into collection bins 904 for the user.

Figure 12A:
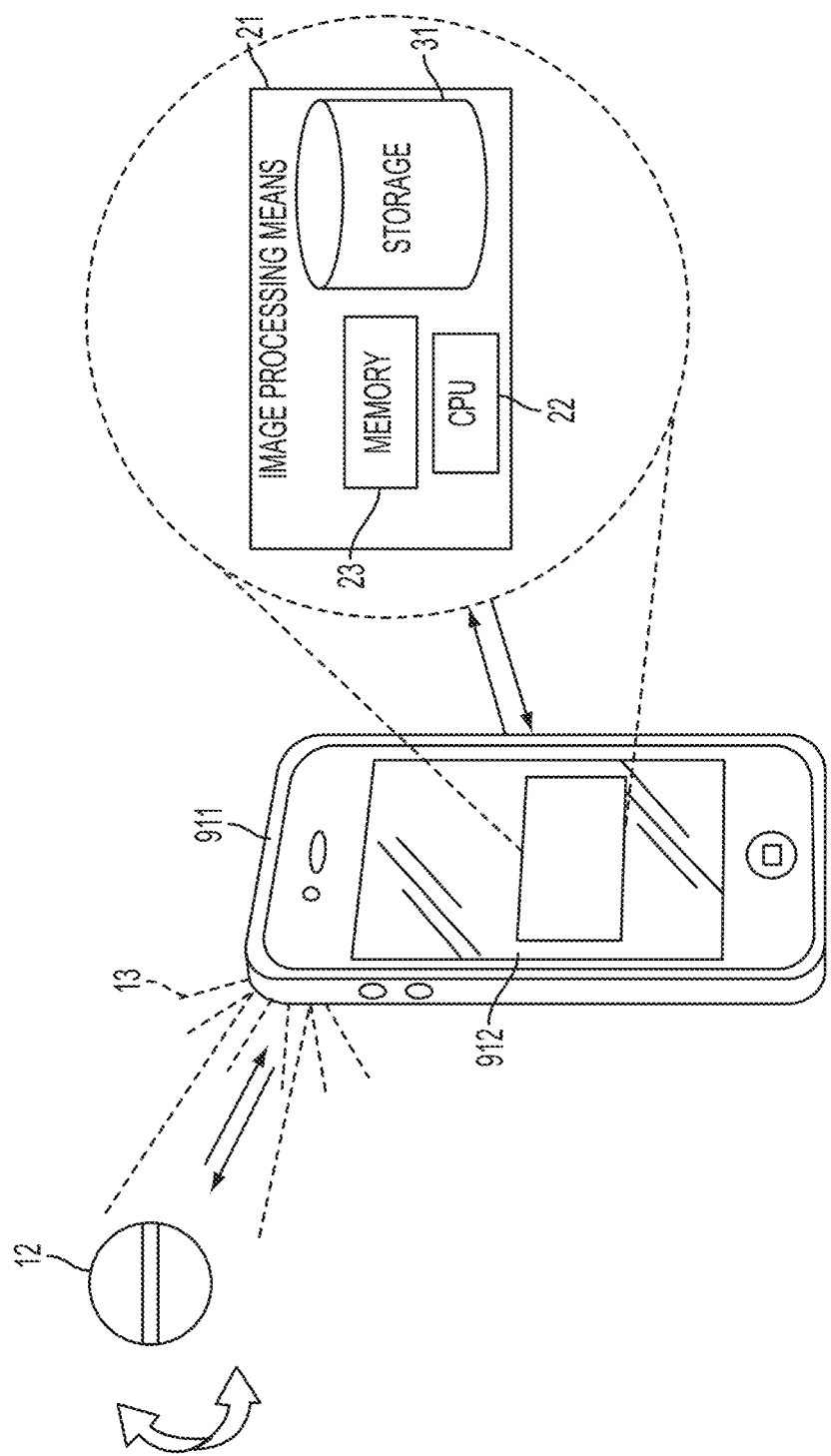
FIG. 12a shows a view of an exemplary embodiment of the present system and method, whereby a handheld device is deployed to capture and process the medicine image.
Figure 12B:
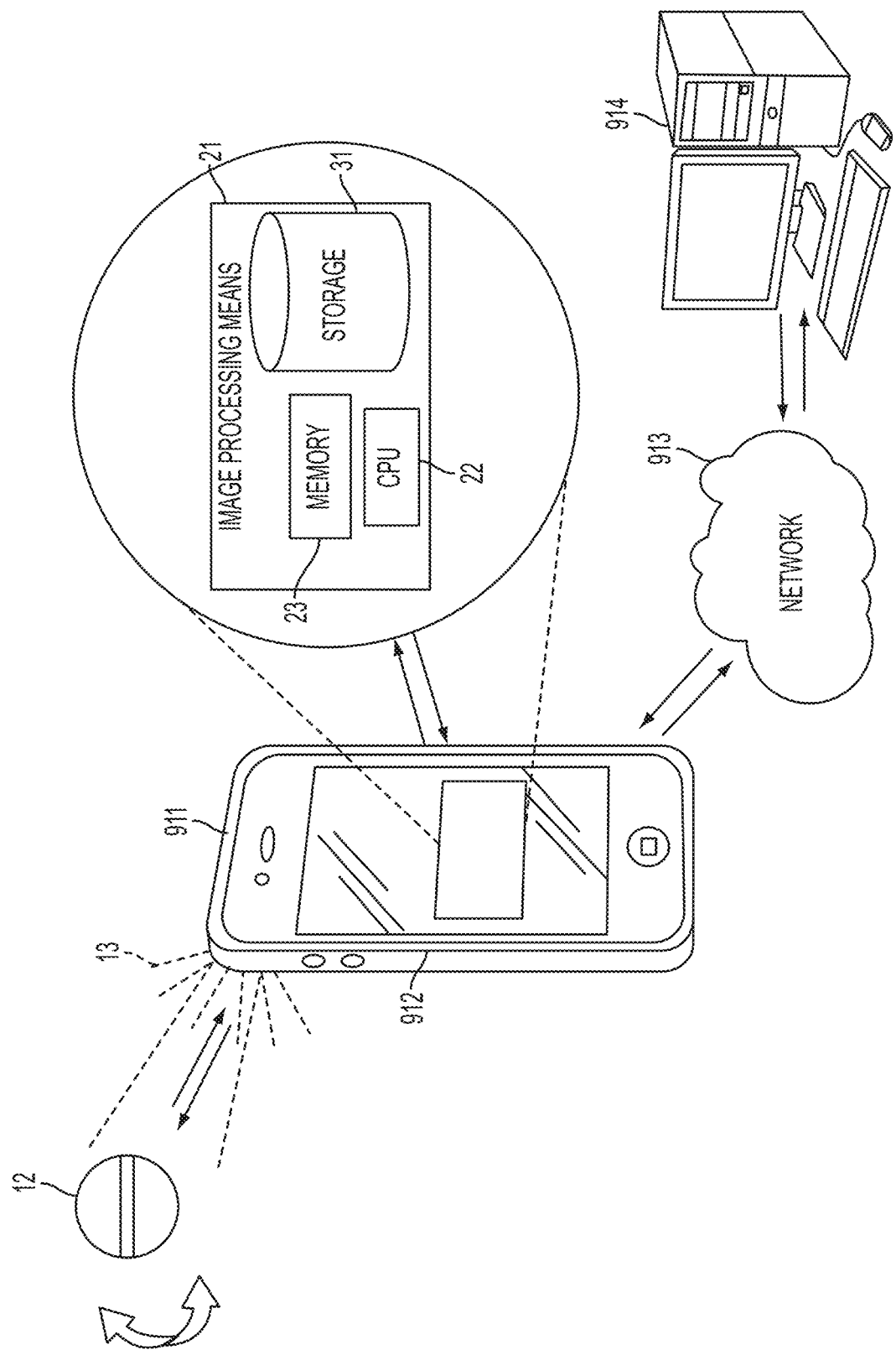
FIG. 12b shows a view of an exemplary embodiment of the present system and method, whereby a handheld device is deployed to capture and process the medicine image using access to a remote server.

Referring now to FIGS. 12*a* and 12*b*, there is shown an embodiment of the present system in which a handheld electronic device or smartphone device 911 is employed as a means of capturing and processing a target medicine 12 image. In this embodiment, the handheld device 911 incorporates the image processing unit 21 and the image capture unit of the system. Notably, a camera 13 along the device 911 allows a user to capture an image of the target medicine 12, store the image onto the local storage means 31 within the device 912 while controlling the process through an application on the device interface 912. The image processing unit 21 proceeds as with the sorting embodiment, wherein the target medicine is captured as an input image to be compared against reference images stored within a database. The database may be stored locally on the device storage means 31, or alternatively the device may have network 701 connectivity. With connectivity to a network 913 using a network interface means (e.g. a wireless antenna chip or Ethernet port), the database can be stored on a remote server 914, reducing the storage needs of the device 911 and relying on the remote server 914 to store the files of the reference medicine images. The network may comprise an internet network, a local area network, or a wireless network. A further embodiment and a variation to that configuration shown in FIG. 12*b* is the option for running the image processing unit 21 on the remote server 914, as opposed to running the processing means 21 locally on the handheld electronic device 911. This embodiment allows the processing of the medicine 12 to occur remotely, where improved computing power may be employed over that installed in the handheld device 911. The image is therefore processed remotely and the results of the information are relayed back through the network 913 for the handheld device to relay results to the user. This embodiment is particularly useful to law enforcement officers, first responders or generally to anyone who may need to identify a medicine immediately without much effort other than capturing the image of a not-readily-identifiable medicine with a smart phone or the like.

Medicine Data Display

Once a medicine is identified, the system of the subject technology provides visual notification of the medicine identity as well as additional data that may be customized according to the user's need. The medicine identity data and information can be visualized through a screen (e.g., smart phone screen, a monitor, TV screen and the like). In an embodiment, the user may customize the information that can be displayed by the system and method of the subject technology. For example, an emergency responder may customize the system or device of the subject technology such that any of the following information is displayed: the medicine image; the medicines active ingredient, i.e., the drug contained with the medicine; the drug's major function, the drugs possible side effect, what the steps that must be taken in case of overdose or abuse; and/or the drug's antidote. See Table 1 below:

TABLE 1

| Drug Image | |
|---|---|
| Drug's Name | Hydrocodone/Acetaminophen (Vicodin ®); RX or Prescription drug |
| Active Agent/Ingredient | Combination of: Acetaminophen, Hydrocodone |
| Drug's class: | Analgesic (Pain Reliever), opioid |
| Drug Overdose Sign & Symptoms | Extreme sleepiness Breathing problems Small pupils -- the black circle in the colored part of your eye |
| Drug Antidoe | Oxygen gas: for better breathing; Naloxoane (Narcan ®): only if breathing is seriously compromized; Activated charcoal with a laxative to soak up drug that is still left in your stomach or intestines. Tylenol ® or aspirin: if overdose is suspected but no serious symptom exists |
| Pregnancy Risk | Category C (Risk cannot be ruled out) |
| Drug's Possible Side Effects: | Sedating, habit-forming, dizziness, nausea and vomiting, impaired thinking and function |

On the other hand, a law enforcement officer may only be interested in determining whether the medicine is illicit or not. See Table 2 below:

TABLE 2

| Drug Image | |
|---|---|
| Drug's Name | Ecstasy |
| Illicit - Controlled Substance | YES[1] |

[1]A positive ID may accompany other forms of alarms or notifications.

Sorting or Queuing System

As discussed above with reference to FIG. 11A, the target medicines are either placed within the deposit area 902 manually and one-by-one, or alternatively a sorting or queuing means which can accept a plurality of medicines at once and convey them individually into the identification chamber is used. An exemplary operation of the sorting and queuing system of the subject technology is described below.

Figure 13:
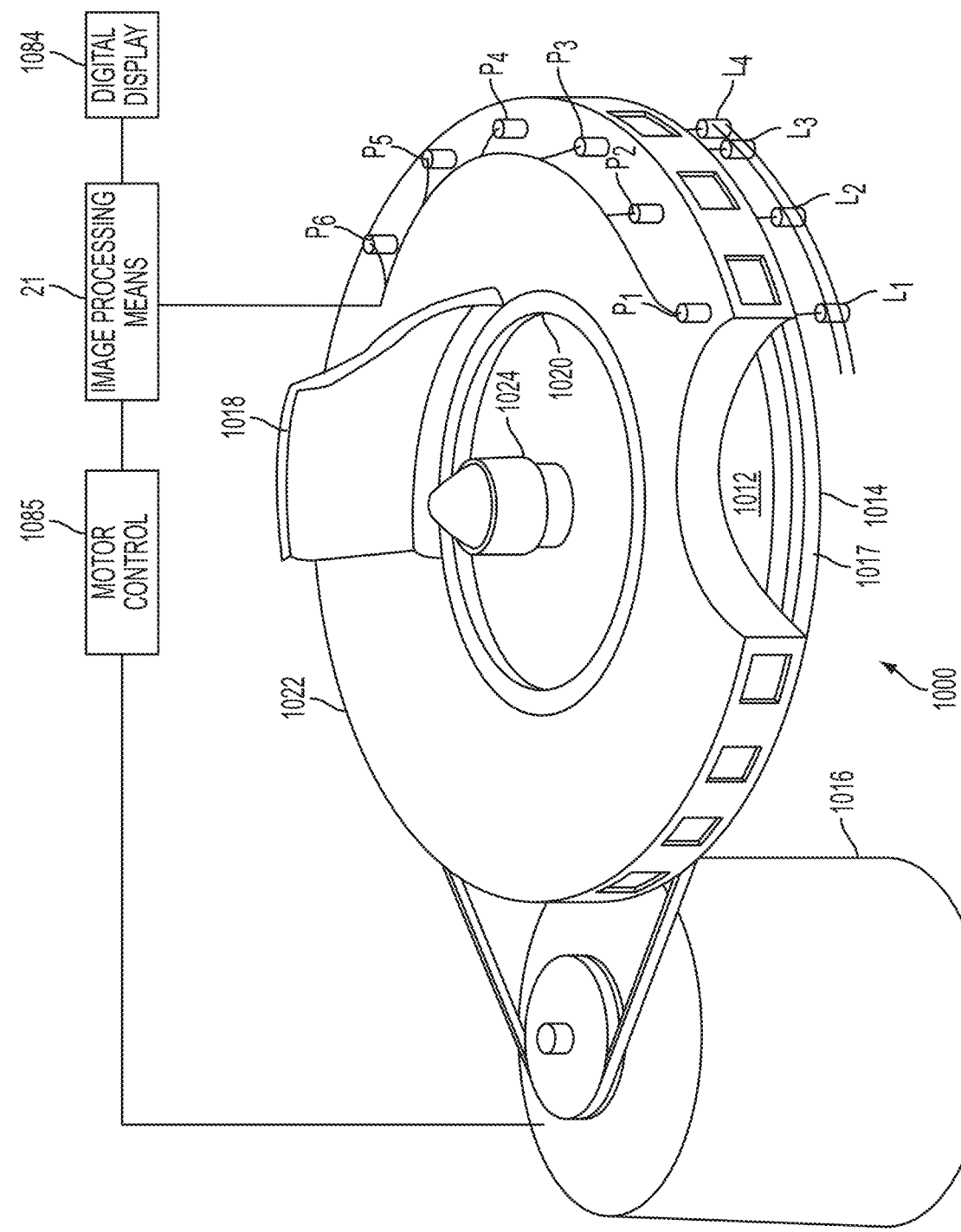
FIG. 13 is a pictorial view of a configuration of an exemplary embodiment of the subject technology in which a sorting and queuing apparatus is shown.
Figure 14:
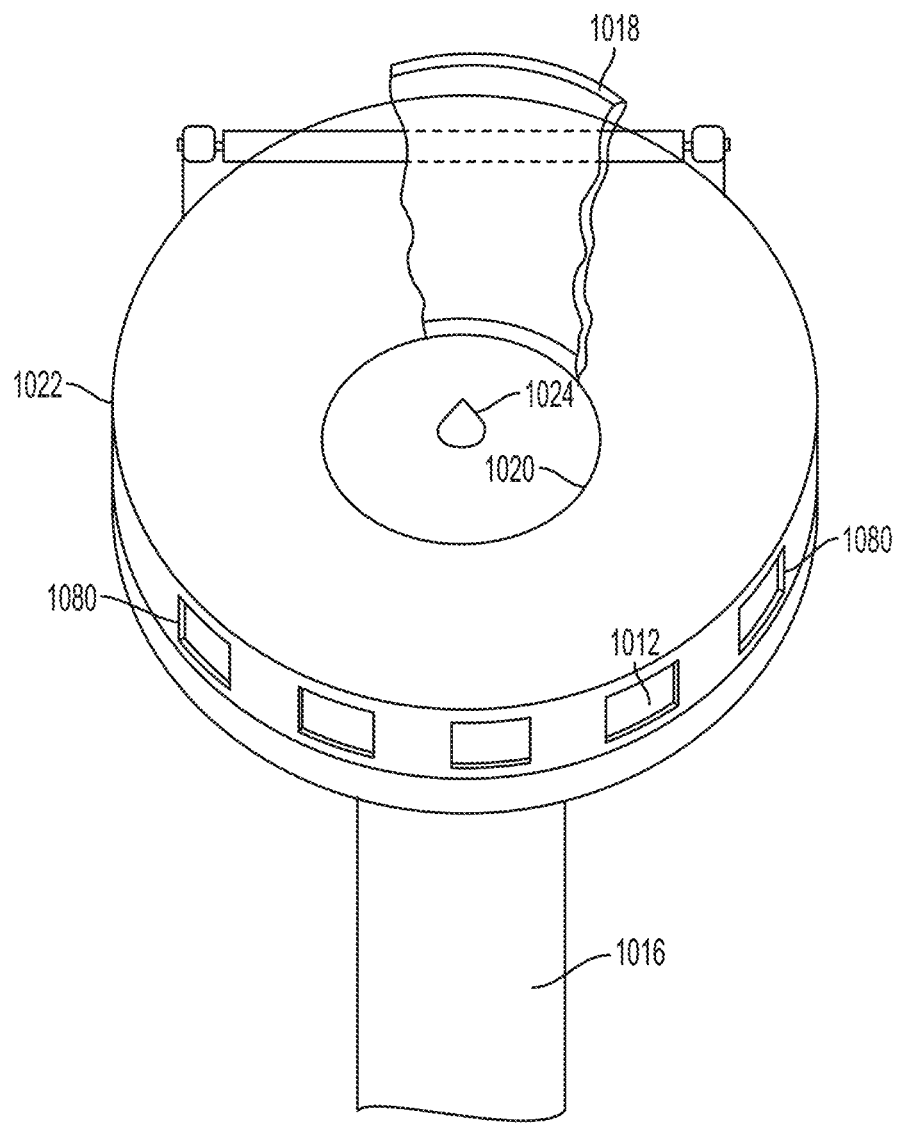
FIG. 14 is another rendition of the sorting and queuing apparatus in accordance with an exemplary embodiment of the subject technology.
Figure 20:
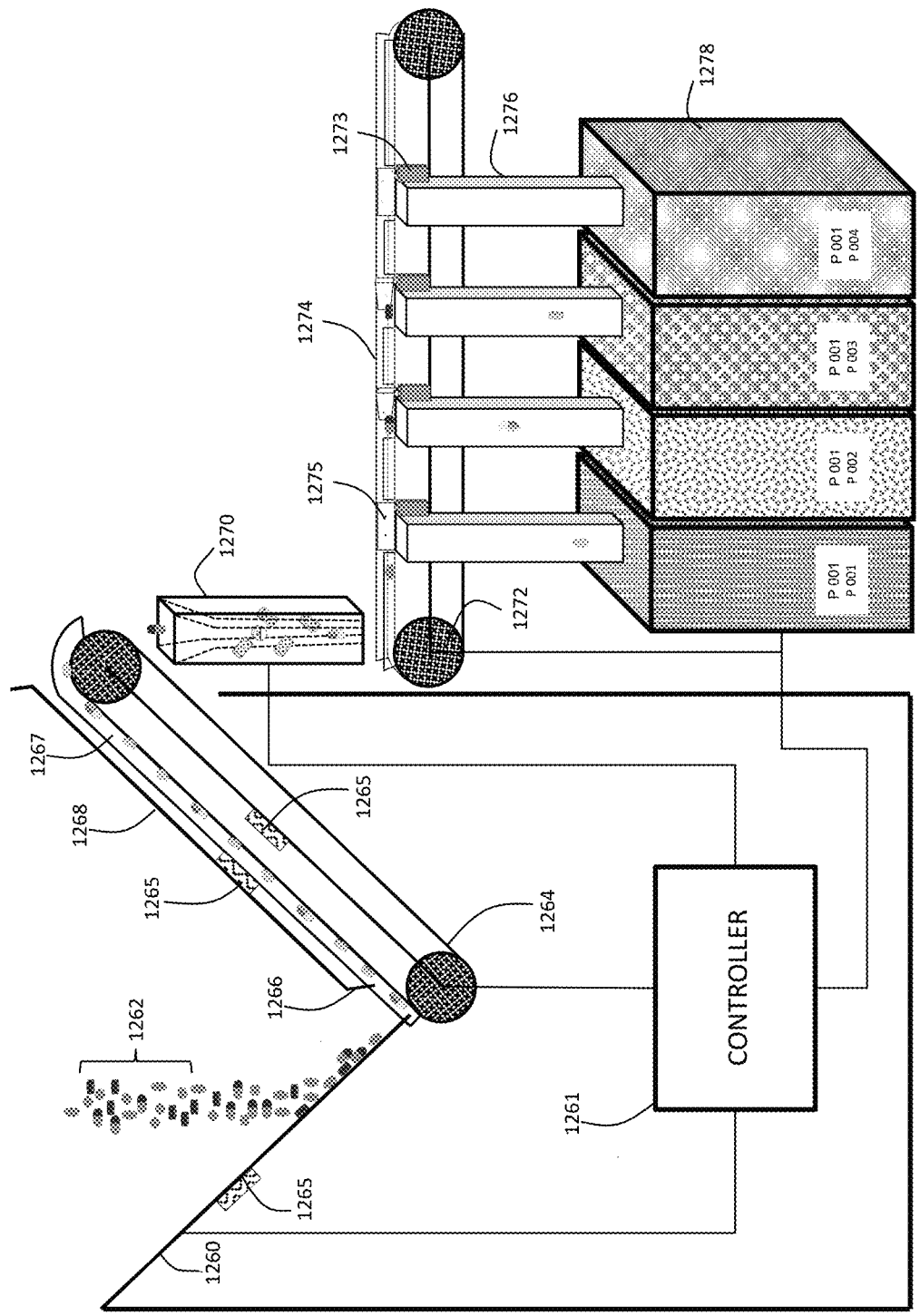
FIG. 20 illustrates an exemplary medicine identification and sorting device or system for receiving, queuing, identifying and sorting mixed medicines.

Referring initially to FIG. 13, basically, the exemplary sorter 1000 employs a resilient disc in the form of pad 1012 of a rigid or an elastomer construction rotated on and by a turntable 1014 driven by motor 1016 via belt 1017. A hopper 1018 (shown as partially broken away) is positioned about an opening 1020 in guide plate 1022, and medicines to be sorted are inserted through this hopper. Guide plate 1022 is supported, by means not shown, at a selected spacing (e.g., from about 0.001 mm to 100 mm) with respect to pad 1012, typically about 0.02 to about 30 mm. A centrally positioned hub 1024 extends through an opening (not shown) in pad 1012 and is conventionally secured as by a threaded connection to turntable 1014. Hub 1024 has a tapered surface which functions to direct medicines in an off-center direction so that there will always be some centrifugal force tending to cause medicines to move outward toward guide plate 1022. In FIG. 14, another exemplary sorter 1000 is show in which the pad 1012 is driven by motor 1016 located below the sorter. The guide plate 1022 is positioned above the pad and is supported by hinges which allow the easy opening and closing of the sorter. Another exemplary sorter is shown in FIG. 20.

Figure 15A:
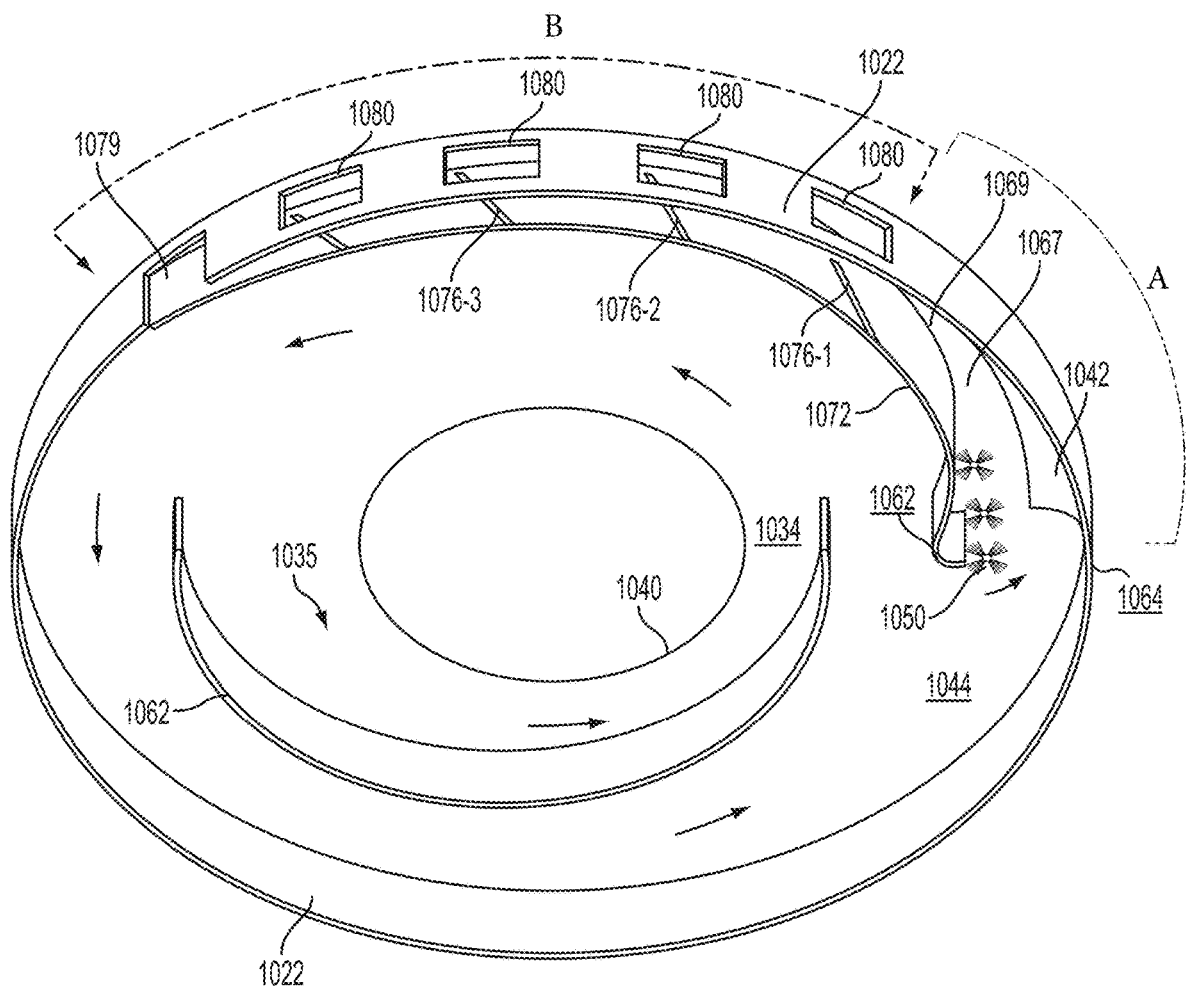
FIG. 15A is an exemplary bottom or underside view of an exemplary guide plate of the subject technology, which controls the movement of medicines before they are introduced to the medicine identification chamber or unit.
Figure 15B:
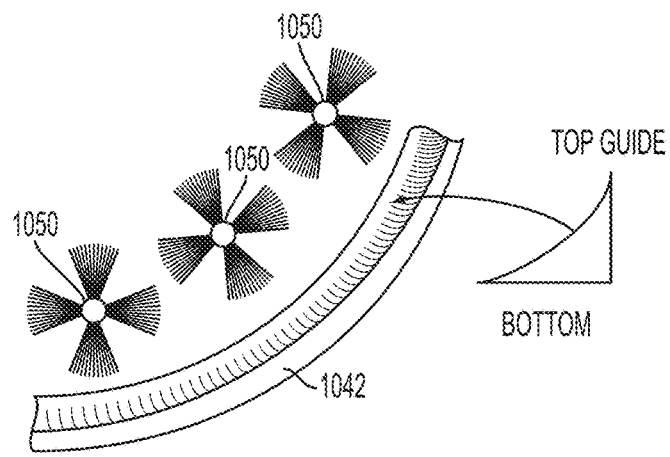
FIG. 15B is an exemplary illustration showing section A of guide plate 1022 depicted in FIG. 15A.

Referring now additionally to FIG. 15, the underside of guide plate 1022 is configured to guide medicines rotated by pad 1012 to move in the direction of the arrows in a circular and then spiral path outward within an inner positioned recess 1034 which overall is oval in configuration and has an inner guide, or guide edge 1030, which extends around it. The medicines are moved outward by centrifugal force; and are moved in a path governed by tapered inner facing edge 1030 of recess 1034, this recess having, in general, a depth on the order of 0.05 to 30 millimeter or deeper than the thickest medicine to be sorted. Thus, the medicines are free on the top surface of recess 1034. The first part of their travel is generally circular and during it the medicines are formed in a single file.

At approximately point 1040, edge 1030 of recess 1034 transitions, in a recess portion 1044, from being circular to a spiral, and thereafter medicines are moved outward, along edge 1042, by the combination of circular movement of pad 1012 and centrifugal force. Recess region 1044 may be of the same depth as other portions of recess 1034 or slightly shallower. Where it is necessary to provide reduced depth, there would be a gradual transition or slight ramp downward between central portion 1035 of recess 1034 and recess region or portion 1044 and downwardly between recess region 1044 and region 1067, with reference to a counter-clockwise direction of FIG. 15. In some embodiments, there is no reduced depth anywhere in the portions 1035, 1044 or 1067; and they all will have the same depth. In some embodiments, one or more circular bushes are installed along the path A between the recess portions 1044 and 1067 to facilitate the movement of the medicines along this path, or to break any bottlenecking that may have occurred in the recess 1044 portion, or to cause medicines to move individually and in a single file along the path A. Particularly, where there is a possibility that one medicine may be on top of another medicine as they move to the portion 1044, the movement of the brush(es) 1050, which is either slower or faster than the rotational movement of the pad 1012, will urge the piggybacked medicines to disengage from one another and to move in a single file and behind each other as they move through area A of FIG. 15. Also, if a medicine is standing on its side as it enters the portion 1044, the action of the brush(es) together with the inclined shape of the edge 1042 will urge the medicine to lay flat as it enters the area A of FIG. 15. Medicines that will not enter the recess portion 1044 will be re-circulated around pad 1012 until they get the chance to enter the portion 1044. Thus, recess portion 1044 also forms a restricted passageway for a single file of medicines. This passageway is formed between outward projection 1062 and edge 1064 of recess 1044.

As the pad 1012 rotates, medicines are moved outwardly into the recess portion 1044 and thereby move around the guide edge 1062 until they are moved circularly beyond the recess portion 1044 of the recess 1034 where they are free to move outwardly by centrifugal force. Freely moving medicines finally form a single file in the recess portion 1067 and are rotated by pad 1012 to a peripheral area from point 1069 to point 1079 (i.e., area B in FIG. 15, panel A) containing a plurality of medicine ejection ramps which are each distinctively configured to eject a discrete diameter of medicine, the largest being ejected first. From point 1069 to point 1079, medicines come in contact with upwardly extending ramps 1076-1 to 1076-*n* (FIGS. 15-16) based on their maximum diameter (in case of round tablets) or width (in case of capsules, caplets, oval, oblong or polygonal tablets) or simply the maximum width they occupy on the pad 1012.

Figure 16:
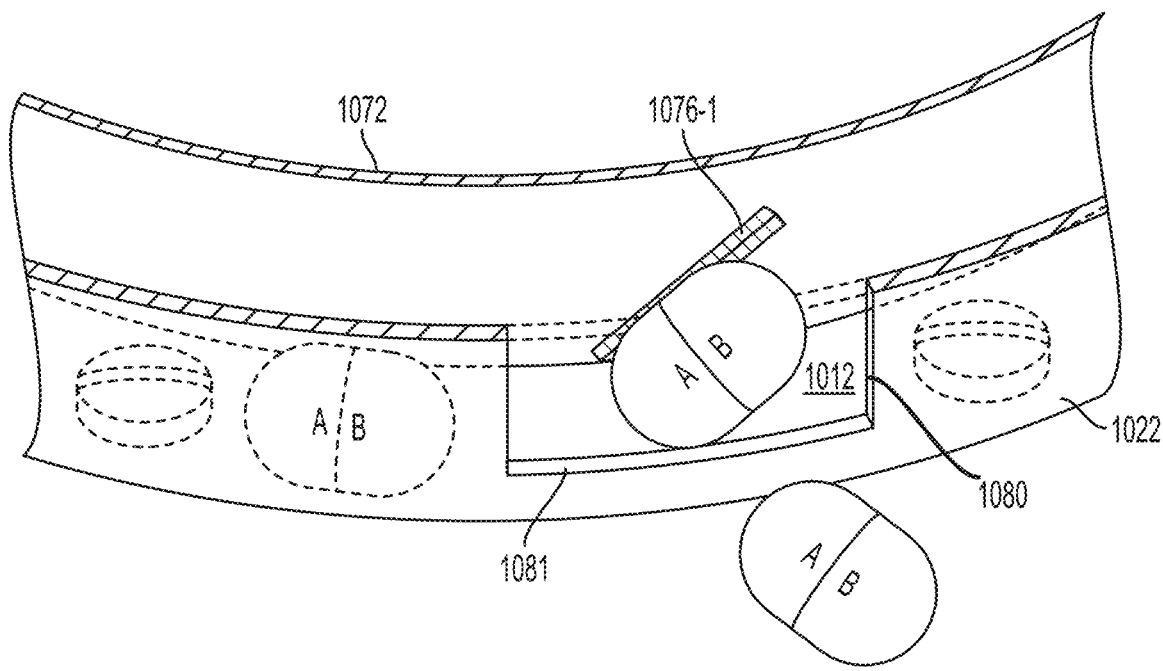
FIG. 16 is a pictorial view showing a ramp and window portion of the guide plate of FIG. 15A with an added illustration of the movement of medicine AB as it is moving on pad 1012 and being ejected from the guide plate by one of the ramps 1076.

The ramps 1076-1 to 1076-*n* are disposed on the edge 1072 facing the windows 1080 around the outer edge of the guide plate 1022. Lines designated as in FIG. 17 (or X1-X4 in FIG. 17B) indicates a maximum diameter of the circular path at any given ramp (1076-1 to 1076-*n*) along which medicines may progress. This width or diameter, X, gradually narrows or tapers from the ramp 1076-1 to the ramp 1076-*n*. Due to the centrifugal force being applied to the medicines, for example, a medicine AB (FIG. 16) is urged outward along edge 1042 to point 1069 (FIG. 15A) where the medicine AB comes in between the outer edge of the guide plate 1022 and the first ramp 1076-1. Once the medicine AB arrives at a position where its maximum diameter or width is larger than X, the force exerted by the outer edge of the guide plate 1022 (which is equal but opposite in direction to the centrifugal force generated by the rotating pad 1012) urges the medicine AB to go over the ramp 1076 (e.g., any of 1076-1 to 1076-*n*). This action causes the medicine to be lifted up from the pad 1012 and ejected out of the sorter 1000 through the windows 1080 (FIGS. 14 and 16). If a medicine is not engaged with a ramp because of its diameter is less than $X_n$ of that ramp, the centrifugal force that is applied to the medicine by the rotational movement of the pad 1012 is not sufficient to cause the medicine to be ejected out the windows 1080 without having gone over the ramps.

If a medicine's diameter or width is less than X at a given ramp, the medicine will simply pass that ramp without going over it; and as such it will not be ejected out of the window 1080. For example, if, while traveling from point 1069 to point 1079 (FIG. 15), a medicine such as a round tablet happens to be sanding on its side while moving forward, this medicine will finally go over a ramp at which the thickness of the table (as the table is sanding on its side) is larger than the X at that ramp. The windows 1080 have a low beveled edge 1081 at the bottom (FIG. 16) which will prevent medicines to exit the sorter 1000 without being first engaged with the ramps. In one embodiment, the guide plate has a low beveled edge all around the outer periphery. The guide plate 1022 is designed so that the largest medicine exits the sorter 1000 first and the smallest medicine exits the sorter 1000 last. The diameter X at the ramp 1076-*n* may be zero millimeter or close to zero mm so that any powder or crushed medicine that may be on the pad 1012 will exit the window opposite to this last ramp. The window opposite to ramp 1076-*n* (the last ramp) therefore may not have a bottom edge to facilitate the exit of the powdered materials from this window. This action of the last ramp will assist in a continuous cleaning of the surface of the pad 1012.

Figure 17A:
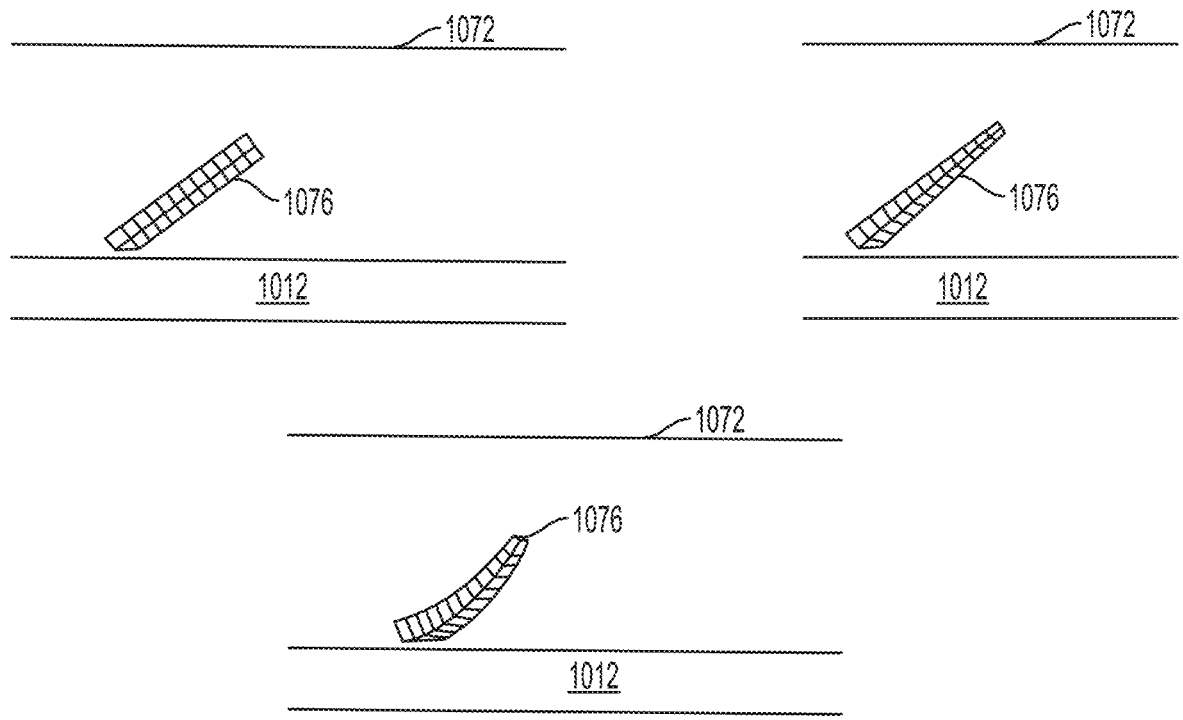
FIG. 17A shows various exemplary ramps of the guide plate of FIG. 15A
Figure 17B:
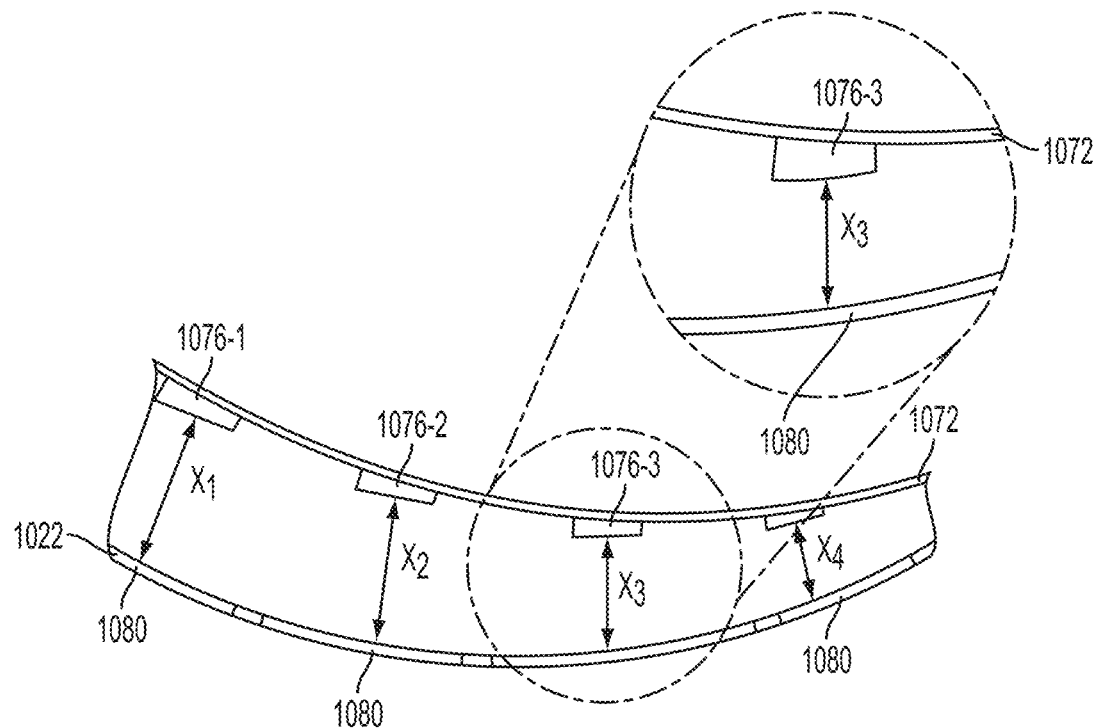
FIG. 17B is a top view of the periphery of an exemplary sorter of the subject technology, in which four exemplary ramps which face the guide plate windows are shown.

Referring to FIGS. 17A and B, in various exemplary embodiments, each ramp includes a blade projecting outwardly from the edge 1072 and extending upwardly away from the pad 1012 with a slope of variable degree angles with respect to the pad 1012. In an exemplary embodiment, the ramp has a slope of 3 to 75 degrees with respect to the pad 1012. The ramp may be straight with a constant slope or may have curves with variable slopes. The outward facing edge of the ramp or blade may extend slightly downwardly or upwardly in the direction of the window 1080 so that a medicine that goes on the ramp is ejected in the direction of the window 1080. The width of the ramp is constant or may be increasing, or both, from the point closest to the pad 1012 to the point farthest from the pad 1012 (FIG. 17A). All the ramps 1076-1 to 1076-*n* may have of the same size and shape (FIG. 17B) or may be of different sizes. For example, the ramp 1076-1 may be larger in size from the other ramps, and the subsequent ramps may progressively get smaller in size from the point 1069 to the point 1079.

In some embodiments, the X value at each ramp ranges from about 30 mm to about 0 mm. In an embodiment, X1 (the X value at ramp 1076-1, FIG. 17B) is about 9 mm, X2 is about 8.5 mm, X3 about 7.5 mm, X4 is about 6.5 mm, X5 is about 6 mm, X6 is about 5 mm, X7 is about 4.5 mm, X8 is about 3.5 mm, X9 is about 2.5 mm. In an aspect related to this embodiment, the ramps 1076-1 to 1076-9 will be able to capture and eject the medicines listed in Table 3 below.

| RX (Brand Name) | Dosage | width/diameter (mm)[1] | X (mm) |
|---|---|---|---|
| Vicoprofen ® | 10 mg | 13.4 | 9 |
| Vicoprofen ® | 50 mg/1000 mg | 11 | 9 |
| Vicoprofen ® | 200 mg | 9.5 | 9 |
| Vicoprofen ® | 140 mg | 9.5 | 9 |
| Vicoprofen ® | 10 mg | 9.5 | 9 |
| Vicoprofen ® | 100 mg | 9.5 | 9 |
| Vicoprofen ® | 12 mg | 9.5 | 9 |
| Vicoprofen ® | 40 mg/25 mg | 9.5 | 9 |
| Vicoprofen ® | 20 mg | 9.5 | 9 |
| Vicoprofen ® | 10 mg | 9.5 | 9 |
| Vicoprofen ® | 5 mg | 9.5 | 9 |
| Vicoprofen ® | 7.5 mg/200 mg | 9.5 | 9 |
| Tekturna ® | 150 mg | 9.5 | 9 |
| Saphris ® | 5 mg | 9.5 | 9 |
| Potaba ® | 500 mg | 9.5 | 9 |
| Myfortic ® | 180 mg | 9.5 | 9 |
| Maxalt-MLT ® | 5 mg | 9.5 | 9 |
| EDARBYCLOR ® | 40 mg/12.5 mg | 9.5 | 9 |
| Stribld ® | 550 mg | 9.5 | 9 |
| Stribld ® | 1000 mg | 9.5 | 9 |
| Stribld ® | 5 mg/1000 mg | 9.5 | 9 |
| Stribld ® | 5 mg/500 mg | 9.5 | 9 |
| Stribld ® | 100 mg/1000 mg | 9.5 | 9 |
| Stribld ® | 50 mg/1000 mg | 9.5 | 9 |
| Stribld ® | 500 mg | 9.5 | 9 |
| Stribld ® | 420 mg | 9.5 | 9 |
| Stribld ® | 1.0 mg | 9.5 | 9 |
| Stribld ® | 150 mg/150 mg/ 200 mg/300 mg | 9.5 | 9 |
| Norvir ® | 100 mg | 9.5 | 9 |
| Kombiglyze XR ® | 2.5 mg/1000 mg | 9.5 | 9 |
| Janumet XR ® | 50 mg/500 mg | 9.5 | 9 |
| Atripla ® | 600 mg/200 mg/ 300 mg | 9.5 | 9 |
| Xifaxan ® | 80 mg | 8.7 | 8.5 |
| Xifaxan ® | 5 mg | 8.7 | 8.5 |
| Xifaxan ® | 80 mg | 8.7 | 8.5 |
| Xifaxan ® | 60 mg | 8.7 | 8.5 |
| Xifaxan ® | 100 mg | 8.7 | 8.5 |
| Xifaxan ® | 4 mg | 8.7 | 8.5 |
| Xifaxan ® | 10 mg | 8.7 | 8.5 |
| Xifaxan ® | 80 mg | 8.7 | 8.5 |
| Xifaxan ® | 30 mg | 8.7 | 8.5 |
| Xifaxan ® | 200 mg | 8.7 | 8.5 |
| Juvisync ® | 100 mg/10 mg | 8.7 | 8.5 |
| COARTEM ® | 20 mg/120 mg | 8.7 | 8.5 |
| Vicodin ES ® | 300 mg | 8.7 | 8.5 |
| Vicodin ES ® | 600 mg/25 mg | 8.7 | 8.5 |
| Vicodin ES ® | 600 mg | 8.7 | 8.5 |
| Vicodin ES ® | 1.25 mg | 8.7 | 8.5 |
| Vicodin ES ® | 250 mg | 8.7 | 8.5 |
| Vicodin ES ® | 200 mg | 8.7 | 8.5 |
| Vicodin ES ® | 360 mg | 8.7 | 8.5 |
| Vicodin ES ® | 500 mg | 8.7 | 8.5 |
| Vicodin ES ® | 7.5 mg/750 mg | 8.7 | 8.5 |
| Teveten HCT ® | 600 mg/12.5 mg | 8.7 | 8.5 |
| Teveten ® | 400 mg | 8.7 | 8.5 |
| Norvir ® | 100 mg | 8.7 | 8.5 |
| Lialda ® | 1.2 g | 8.7 | 8.5 |
| DEPAKOTE ER ® | 250 mg | 8.7 | 8.5 |
| Baraclude ® | 0.5 mg | 8.7 | 8.5 |
| Biaxin XL Filmtab ® | 300 mg3 | 8 | 7.5 |
| Biaxin XL Filmtab ® | 500 mg | 8 | 7.5 |
| Viread ® | 70 mg | 7.9 | 7.5 |
| Viread ® | 8 mg | 7.9 | 7.5 |
| Viread ® | 8 mg | 7.9 | 7.5 |
| Viread ® | 10 mg | 7.9 | 7.5 |
| Viread ® | 7 mg | 7.9 | 7.5 |
| Viread ® | 6 mg | 7.9 | 7.5 |
| Viread ® | 5 mg | 7.9 | 7.5 |
| Viread ® | 4 mg | 7.9 | 7.5 |
| Viread ® | 3 mg | 7.9 | 7.5 |
| Viread ® | 2.5 mg | 7.9 | 7.5 |
| Viread ® | 2 mg | 7.9 | 7.5 |
| Viread ® | 150 mg | 7.9 | 7.5 |
| Uloric ® | 40 mg | 7.9 | 7.5 |
| Mevacor ® | 20 mg | 7.9 | 7.5 |
| Gleevec ® | 100 mg | 7.9 | 7.5 |
| COUMAOIN ® | 1 mg | 7.9 | 7.5 |
| Truvada ® | 80 mg | 7.9 | 7.5 |
| Truvada ® | 145 mg | 7.9 | 7.5 |
| Truvada ® | 300 mg/10 mg | 7.9 | 7.5 |
| Truvada ® | 200 mg | 7.9 | 7.5 |
| Truvada ® | 4 mg/240 mg | 7.9 | 7.5 |
| Truvada ® | 2 mg/240 mg | 7.9 | 7.5 |
| Truvada ® | 2 mg/240 mg | 7.9 | 7.5 |
| Truvada ® | 1 mg/240 mg | 7.9 | 7.5 |
| Truvada ® | 1000 mg/20 mg | 7.9 | 7.5 |
| Truvada ® | 750 mg/20 mg | 7.9 | 7.5 |
| Truvada ® | 500 mg | 7.9 | 7.5 |
| Truvada ® | 750 mg | 7.9 | 7.5 |
| Truvada ® | 120 mg | 7.9 | 7.5 |
| Truvada ® | 400 mg | 7.9 | 7.5 |
| Truvada ® | 100 mg | 7.9 | 7.5 |
| Truvada ® | 10 mg/320 mg/ 25 mg | 7.9 | 7.5 |
| Truvada ® | 320 mg/25 mg | 7.9 | 7.5 |
| Truvada ® | 400 mg | 7.9 | 7.5 |
| Truvada ® | 240 mg | 7.9 | 7.5 |
| Truvada ® | 200 mg/300 mg | 7.9 | 7.5 |
| Tarka ® | 2 mg/180 mg | 7.9 | 7.5 |
| Singulair ® | 4 mg | 7.9 | 7.5 |
| Ranexa ® | 500 mg | 7.9 | 7.5 |
| Noroxin ® | 400 mg | 7.9 | 7.5 |
| Janumet ® | 50 mg/500 mg | 7.9 | 7.5 |
| Tradjenta ® | 0.75 mg | 7.1 | 6.5 |
| Tradjenta ® | 20 mg | 7.1 | 6.5 |
| Tradjenta ® | 30 mg | 7.1 | 6.5 |
| Tradjenta ® | 5 mg | 7.1 | 6.5 |
| Tradjenta ® | 75 mg | 7.1 | 6.5 |
| Tradjenta ® | 4 mg | 7.1 | 6.5 |
| Tradjenta ® | 40 mg | 7.1 | 6.5 |
| Tradjenta ® | 50 mg | 7.1 | 6.5 |
| Tradjenta ® | 3 mg | 7.1 | 6.5 |
| Tradjenta ® | 1 mg | 7.1 | 6.5 |
| Tradjenta ® | 15 mg | 7.1 | 6.5 |
| Tradjenta ® | 20 mg | 7.1 | 6.5 |
| Tradjenta ® | 5 mg | 7.1 | 6.5 |
| Samsca ® | 15 mg | 7.1 | 6.5 |
| Propecia ® | 1 mg | 7.1 | 6.5 |
| Prinzide ® | 20 mg/12.5 mg | 7.1 | 6.5 |
| Onglyza ® | 2.5 mg | 7.1 | 6.5 |
| Isentress ® | 25 mg | 7.1 | 6.5 |
| EDARBI ® | 40 mg | 7.1 | 6.5 |
| Vicodin HP ® | 40 mg | 7.1 | 6.5 |
| Vicodin HP ® | 10/80 mg | 7.1 | 6.5 |
| Vicodin HP ® | 250 mg | 7.1 | 6.5 |
| Vicodin HP ® | 135 mg | 7.1 | 6.5 |
| Vicodin HP ® | 250 mg | 7.1 | 6.5 |
| Vicodin HP ® | 300 mg/5 mg | 7.1 | 6.5 |
| Vicodin HP ® | 100 mg | 7.1 | 6.5 |
| Vicodin HP ® | 25 mg | 7.1 | 6.5 |
| Vicodin HP ® | 10 mg | 7.1 | 6.5 |
| Vicodin HP ® | 100 mg | 7.1 | 6.5 |
| Vicodin HP ® | 0.625 mg/5 mg | 7.1 | 6.5 |
| Vicodin HP ® | 0.625 mg/2.5 mg | 7.1 | 6.5 |
| Vicodin HP ® | 0.45 mg/1.5 mg | 7.1 | 6.5 |
| Vicodin HP ® | 100 mg | 7.1 | 6.5 |
| Vicodin HP ® | 360 mg | 7.1 | 6.5 |
| Vicodin HP ® | 400 mg | 7.1 | 6.5 |
| Vicodin HP ® | 40 mg | 7.1 | 6.5 |

| RX (Brand Name) | Dosage | width/diameter (mm)[1] | X (mm) |
|---|---|---|---|
| Vicodin HP ® | 35 mg | 7.1 | 6.5 |
| Vicodin HP ® | 30 mg | 7.1 | 6.5 |
| Vicodin HP ® | 25 mg | 7.1 | 6.5 |
| Vicodin HP ® | 10 mg/320 mg | 7.1 | 6.5 |
| Vicodin HP ® | 5 mg/320 mg | 7.1 | 6.5 |
| Vicodin HP ® | 320 mg/12.5 mg | 7.1 | 6.5 |
| Vicodin HP ® | 320 mg | 7.1 | 6.5 |
| Vicodin HP ® | 500 mg | 7.1 | 6.5 |
| Vicodin HP ® | 200 mg | 7.1 | 6.5 |
| Vicodin HP ® | 180 mg | 7.1 | 6.5 |
| Vicodin HP ® | 150 mg/10 mg/12.5 mg | 7.1 | 6.5 |
| Vicodin HP ® | 300 mg/10 mg/12.5 mg | 7.1 | 6.5 |
| Vicodin HP ® | 300 mg/5 mg/25 mg | 7.1 | 6.5 |
| Vicodin HP ® | 300 mg/5 mg/12.5 mg | 7.1 | 6.5 |
| Vicodin HP ® | 750 mg/20 mg | 7.1 | 6.5 |
| Vicodin HP ® | 15 mg | 7.1 | 6.5 |
| Vicodin HP ® | 10 mg/660 mg | 7.1 | 6.5 |
| Vicodin ® | 5 mg/500 mg | 7.1 | 6.5 |
| Simcor ® | 500 mg/20 mg | 7.1 | 6.5 |
| PRISTIQ ® | 50 mg | 7.1 | 6.5 |
| PREMPRO ® | 0.3 mg/1.5 mg | 7.1 | 6.5 |
| Niaspan ® | 500 mg | 7.1 | 6.5 |
| COMPLERA ® | 200 mg/25 mg/300 mg | 7.1 | 6.5 |
| Avelox ® | 400 mg | 7.1 | 6.5 |
| Apriso ® | 0.375 g | 7.1 | 6.5 |
| Adderall XR ® | 5 mg | 7.1 | 6.5 |
| Letairis ® | 600 mg | 6.7 | 6.5 |
| Letairis ® | 5 mg | 6.35 | 6 |
| Synthroid ® | 300 mcg | 6.3 | 6 |
| Synthroid ® | 200 mcg | 6.3 | 6 |
| Synthroid ® | 175 mcg | 6.3 | 6 |
| Synthroid ® | 150 mcg | 6.3 | 6 |
| Synthroid ® | 137 mcg | 6.3 | 6 |
| Synthroid ® | 125 mcg | 6.3 | 6 |
| Synthroid ® | 112 mcg | 6.3 | 6 |
| Synthroid ® | 100 mcg | 6.3 | 6 |
| Synthroid ® | 88 mcg | 6.3 | 6 |
| Synthroid ® | 75 mcg | 6.3 | 6 |
| Synthroid ® | 50 mcg | 6.3 | 6 |
| Synthroid ® | 40 mg | 6.3 | 6 |
| Synthroid ® | 30 mg | 6.3 | 6 |
| Synthroid ® | 20 mg | 6.3 | 6 |
| Synthroid ® | 15 mg | 6.3 | 6 |
| Synthroid ® | 40 mg | 6.3 | 6 |
| Synthroid ® | 2 mg | 6.3 | 6 |
| Synthroid ® | 2 mg | 6.3 | 6 |
| Synthroid ® | 6 mg | 6.3 | 6 |
| Synthroid ® | 25 mcg | 6.3 | 6 |
| Proscar ® | 5 mg | 6.3 | 6 |
| Oxycontin ® | 10 mg | 6.3 | 6 |
| Intuniv ® | 1 mg | 6.3 | 6 |
| Abilify discmelt ® | 10 mg | 6.3 | 6 |
| Tasigna ® | 80 mg | 6.3 | 6 |
| Tasigna ® | 200 mg | 6.3 | 6 |
| Tasigna ® | 150 mg | 6.3 | 6 |
| Tasigna ® | 140 mg | 6.3 | 6 |
| Tasigna ® | 300 mg/25 mg | 6.3 | 6 |
| Tasigna ® | 300 mg/12.5 mg | 6.3 | 6 |
| Tasigna ® | 300 mg | 6.3 | 6 |
| Tasigna ® | 200 mg | 6.3 | 6 |
| Tasigna ® | 300 mg | 6.3 | 6 |
| Tasigna ® | 200 mg | 6.3 | 6 |
| Tasigna ® | 0.9 mg | 6.3 | 6 |
| Tasigna ® | 0.625 mg | 6.3 | 6 |
| Tasigna ® | 0.45 mg | 6.3 | 6 |
| Tasigna ® | 150 mg | 6.3 | 6 |
| Tasigna ® | 500 mg | 6.3 | 6 |
| Tasigna ® | 150 mg | 6.3 | 6 |
| Tasigna ® | 100 mg | 6.3 | 6 |
| Tasigna ® | 1000 mg | 6.3 | 6 |
| Tasigna ® | 80 mg | 6.3 | 6 |
| Tasigna ® | 100 mg/40 mg | 6.3 | 6 |
| Tasigna ® | 70 mg/5600 IU | 6.3 | 6 |
| Tasigna ® | 20 mg | 6.3 | 6 |
| Tasigna ® | 125 mg | 6.3 | 6 |
| Tasigna ® | 160 mg | 6.3 | 6 |
| Tasigna ® | 250 mg | 6.3 | 6 |
| Tasigna ® | 60 mg | 6.3 | 6 |
| Tasigna ® | 10 mg | 6.3 | 6 |
| Tasigna ® | 1000 mg/40 mg | 6.3 | 6 |
| Tasigna ® | 1000 mg/20 mg | 6.3 | 6 |
| Tasigna ® | 150 mg | 6.3 | 6 |
| PREMARIN ® | 0.3 mg | 6.3 | 6 |
| Nucynta ER ® | 50 mg | 6.3 | 6 |
| Neoral ® | 20 mg | 6.3 | 6 |
| Fosamax Plus D ® | 70 mg/2800 IU | 6.3 | 6 |
| Fosamax ® | 70 mg | 6.3 | 6 |
| DEPAKENE ® | 250 mg | 6.3 | 6 |
| CLARINEX-D 12 HOUR ® | 2.5 mg/120 mg | 6.3 | 6 |
| Cardizem LA ® | 120 mg | 6.3 | 6 |
| Biaxin Filmtab ® | 250 mg | 6.3 | 6 |
| Advicor ® | 500 mg/20 mg (500 mg extended-release niacin, and 20 mg of immediate-release lovastatin) | 6.3 | 6 |
| Spiriva Handihaler ® | 18 mcg | 5.6 | 5 |
| Xarelto ® | 0.5 mg | 5.5 | 5 |
| Xarelto ® | 15 mg | 5.5 | 5 |
| Xarelto ® | 4 mg | 5.5 | 5 |
| Xarelto ® | 2 mg | 5.5 | 5 |
| Xarelto ® | 15 mg | 5.5 | 5 |
| Xarelto ® | 10 mg | 5.5 | 5 |
| Sprygel ® | 20 mg | 5.5 | 5 |
| Nucynta ® | 50 mg | 5.5 | 5 |
| Mavik ® | 1 mg | 5.5 | 5 |
| Latuda ® | 20 mg | 5.5 | 5 |
| Januvia ® | 25 mg | 5.5 | 5 |
| Femara ® | 2.5 mg | 5.5 | 5 |
| CLARINEX ® | 5 mg | 5.5 | 5 |
| Azilect ® | 0.5 mg | 5.5 | 5 |
| Trilipix ® | 20 mg | 5.5 | 5 |
| Trilipix ® | 4 mcg | 5.5 | 5 |
| Trilipix ® | 2 mcg | 5.5 | 5 |
| Trilipix ® | 100 mg | 5.5 | 5 |
| Trilipix ® | 20 mg | 5.5 | 5 |
| Trilipix ® | 150 mg/25 mg | 5.5 | 5 |
| Trilipix ® | 150 mg/10 mg | 5.5 | 5 |
| Trilipix ® | 150 mg | 5.5 | 5 |
| Trilipix ® | 100 mg/20 mg | 5.5 | 5 |
| Trilipix ® | 4 mg | 5.5 | 5 |
| Trilipix ® | 2 mg | 5.5 | 5 |
| Trilipix ® | 15 mg | 5.5 | 5 |
| Trilipix ® | 10 mg | 5.5 | 5 |
| Trilipix ® | 10 mg/160 mg/25 mg | 5.5 | 5 |
| Trilipix ® | 5 mg/160 mg/25 mg | 5.5 | 5 |
| Trilipix ® | 10 mg/160 mg/12.5 mg | 5.5 | 5 |
| Trilipix ® | 80 mg | 5.5 | 5 |
| Trilipix ® | 100 mg | 5.5 | 5 |
| Trilipix ® | 160 mg/25 mg | 5.5 | 5 |
| Trilipix ® | 160 mg/12.5 mg | 5.5 | 5 |
| Trilipix ® | 60 mg | 5.5 | 5 |
| Trilipix ® | 24 mcg | 5.5 | 5 |
| Trilipix ® | 45 mg | 5.5 | 5 |
| Tricor ® | 48 mg | 5.5 | 5 |
| Tekamlo ® | 150 mg/5 mg | 5.5 | 5 |
| Soriatane ® | 10 mg | 5.5 | 5 |
| Reyataz ® | 100 mg | 5.5 | 5 |
| Pentasa ® | 250 mg | 5.5 | 5 |

-continued

| RX (Brand Name) | Dosage | width/diameter (mm)[1] | X (mm) |
|---|---|---|---|
| Focalin XR ® | 5 mg | 5.5 | 5 |
| EXFORGE HCT ® | 5 mg/160 mg/12.5 mg | 5.5 | 5 |
| DEXILANT ® | 30 mg | 5.5 | 5 |
| DEPAKOTE ® | 125 mg | 5.5 | 5 |
| Crixivan ® | 100 mg | 5.5 | 5 |
| Amturnide ® | 150 mg/5 mg/12.5 mg | 5.5 | 5 |
| Amitiza ® | 8 mcg | 5.5 | 5 |
| Zortress ® | 4 mg | 4.7 | 4.5 |
| Zortress ® | 0.25 mg | 4.7 | 4.5 |
| Livalo ® | 1 mg | 4.7 | 4.5 |
| FANAPT ® | 1 mg | 4.7 | 4.5 |
| DILAUDID ® | 2 mg | 4.7 | 4.5 |
| Bystolic ® | 2.5 mg | 4.7 | 4.5 |
| Zocor ® | 10 mg | 4.7 | 4.5 |
| Zocor ® | 10/40 mg | 4.7 | 4.5 |
| Zocor ® | 10/20 mg | 4.7 | 4.5 |
| Zocor ® | 100 mg | 4.7 | 4.5 |
| Zocor ® | 50 mg | 4.7 | 4.5 |
| Zocor ® | 290 mcg | 4.7 | 4.5 |
| Zocor ® | 9 mg | 4.7 | 4.5 |
| Zocor ® | 6 mg | 4.7 | 4.5 |
| Zocor ® | 3 mg | 4.7 | 4.5 |
| Zocor ® | 10 mg/160 mg | 4.7 | 4.5 |
| Zocor ® | 80 mg | 4.7 | 4.5 |
| Zocor ® | 30 mg | 4.7 | 4.5 |
| Zocor ® | 5 mg | 4.7 | 4.5 |
| Zemplar ® | 1 mcg | 4.7 | 4.5 |
| Temodar ® | 5 mg | 4.7 | 4.5 |
| Tekturna HCT ® | 150 mg/12.5 mg | 4.7 | 4.5 |
| Sustiva ® | 50 mg | 4.7 | 4.5 |
| PRADAXA ® | 75 mg | 4.7 | 4.5 |
| Linzess ® | 145 mcg | 4.7 | 4.5 |
| Invega ® | 1.5 mg | 4.7 | 4.5 |
| EXFORGE ® | 5 mg/160 mg | 4.7 | 4.5 |
| EMEND ® | 40 mg | 4.7 | 4.5 |
| DIOVAN HCT ® | 80 mg/12.5 mg | 4.7 | 4.5 |
| CYMBALTA ® | 20 mg | 4.7 | 4.5 |
| Afinitor ® | 5 mg | 4.7 | 4.5 |
| DALIRESP ® | 500 mg | 3.9 | 3.5 |
| Zolinza ® | 70 mg | 3.9 | 3.5 |
| Zolinza ® | 60 mg | 3.9 | 3.5 |
| Zolinza ® | 50 mg | 3.9 | 3.5 |
| Zolinza ® | 40 mg | 3.9 | 3.5 |
| Zolinza ® | 30 mg | 3.9 | 3.5 |
| Zolinza ® | 10 mg | 3.9 | 3.5 |
| Zolinza ® | 10 mg | 3.9 | 3.5 |
| Zolinza ® | 100 mg | 3.9 | 3.5 |
| Vyvanse ® | 20 mg | 3.9 | 3.5 |
| Vytorin ® | 10/10 mg | 3.9 | 3.5 |
| Vimpat ® | 50 mg | 3.9 | 3.5 |
| DYRENIUM ® | 50 mg | 3.9 | 3.5 |
| DEPAKOTE SPRINKLE ® CAPSULES | 125 mg | 3.9 | 3.5 |
| COLCRYS ® | 0.6 mg | 3.9 | 3.5 |
| Maxalt ® | 10 mg | 3.2 | 2.5 |
| Maxalt ® | 5 mg | 3.2 | 2.5 |
| Maxalt ® | 5 mg | 3.2 | 2.5 |
| Abilify ® | 2 mg | 3.2 | 2.5 |
| Zetia ® | 10 mg | 3.1 | 2.5 |
| DIOVAN ® | 40 mg | 3.1 | 2.5 |

[1] These dimensions are based on a visual inspection of actual-size pictures of the medicines available in the PDR 2014 Edition of Nurse's Drug Handbook.

In one embodiment, the identification and sorting apparatus 901 (FIG. 11A) is placed in front of each of the windows 1080 (except maybe the last window opposite to the last ramp) to capture the medicines exiting or being ejected out of the sorter 1000. Based on the information in Table 3, for example, it is possible to know which medicines are most probable to exit which windows. This knowledge will facilitate or improve the image analysis and computational time required for identification of the medicines traveling through the identification chamber 202 (FIG. 11A).

In some embodiments, additional image capturing devices 13 (in FIG. 1) are installed on the sorter 1000 (e.g., imagers P1-P6 in FIG. 13), for example, on the top of the guide plate 1022 above ramps. A series of lights L1-L4 (only four shown in FIG. 13) may also be installed near the guide plate (above, below or in front of it) to facilitate the imaging of the medicines. Additional sensors may be installed near each of the windows 1080 to count the medicines as they exit the sorter 1000. The output of the imagers P1-P6 or the sensors would be fed to, image processing device 21 (in FIG. 1) or the characterizer 520 (FIG. 7) or displayed on, a conventional digital display (e.g., 590 in FIG. 7). To image the medicines at the sorter 1000 stage, the entire or partial structure of the sorter 1000 including the pad 1012 and the guide plate 1022 (FIG. 13) may be made of transparent plastic or thermoplastic such as Plexiglas® or Lexan®. In one embodiment, the transparent surface in the sorter 1000 is constructed of scratch resistant, optical grade glass such as Corning® Gorilla® Glass.

Medicine Processing Machine

Figure 18:
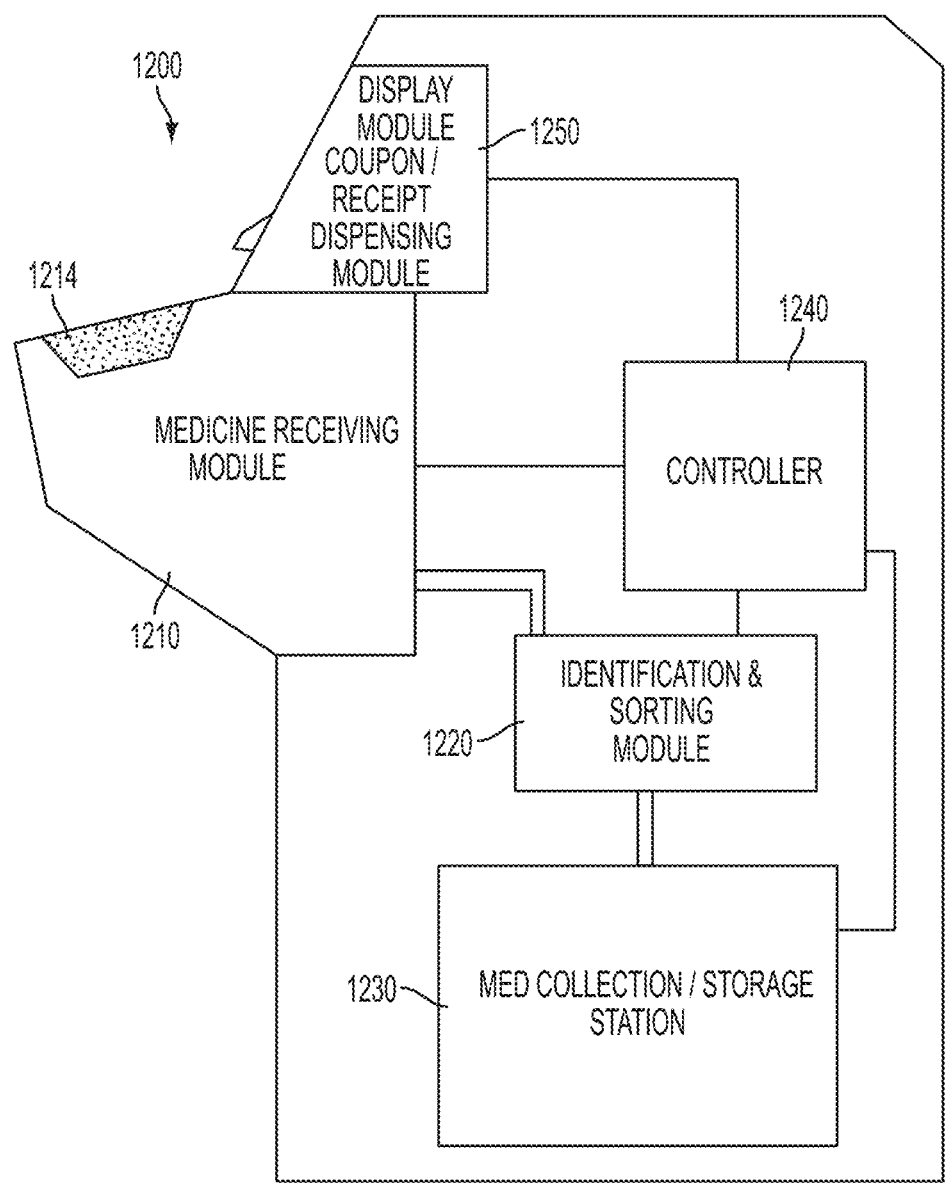
FIG. 18 is an exemplary side view of the medicine processing machine of the present disclosure with its various modules.

FIG. 18 shows an exemplary medicine-processing machine 1200 of the subject technology in a side view illustrating its various modules. The medicine processing machine includes medicine receiving module 1210 which is designed to receive loose medicines or a mixture thereof deposited in the medicine input receptacle 1214. From the module 1210, medicines are transported directly into the identification and sorting module 1220, which includes the identification and sorting system of the subject technology. Medicines are sorted and identified in the module 1220, from which they are distributed to the collections bins of the medicine collection/storage station 1230. A controller 1240 is coupled to each module within the medicine-processing machine 1200 and controls the interaction between each module. For example, the controller 1240 reviews the output sorting and identification data from modules 1220 and 1230 and displays them on the display module 1250 and cause the display module to dispense discount coupons or receipts to the customer.

Figure 11B:
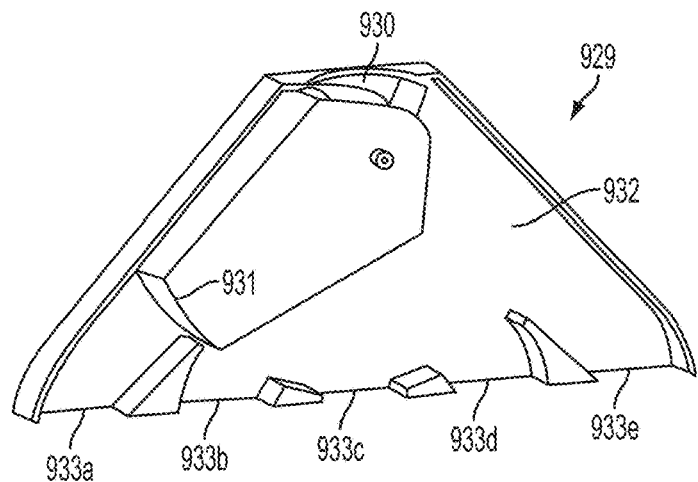
FIG. 11B. is a perspective view of another alternative embodiment of a linear medicine distribution manifold for a medicine processing machine according to an embodiment of the present subject technology.
Figure 19:
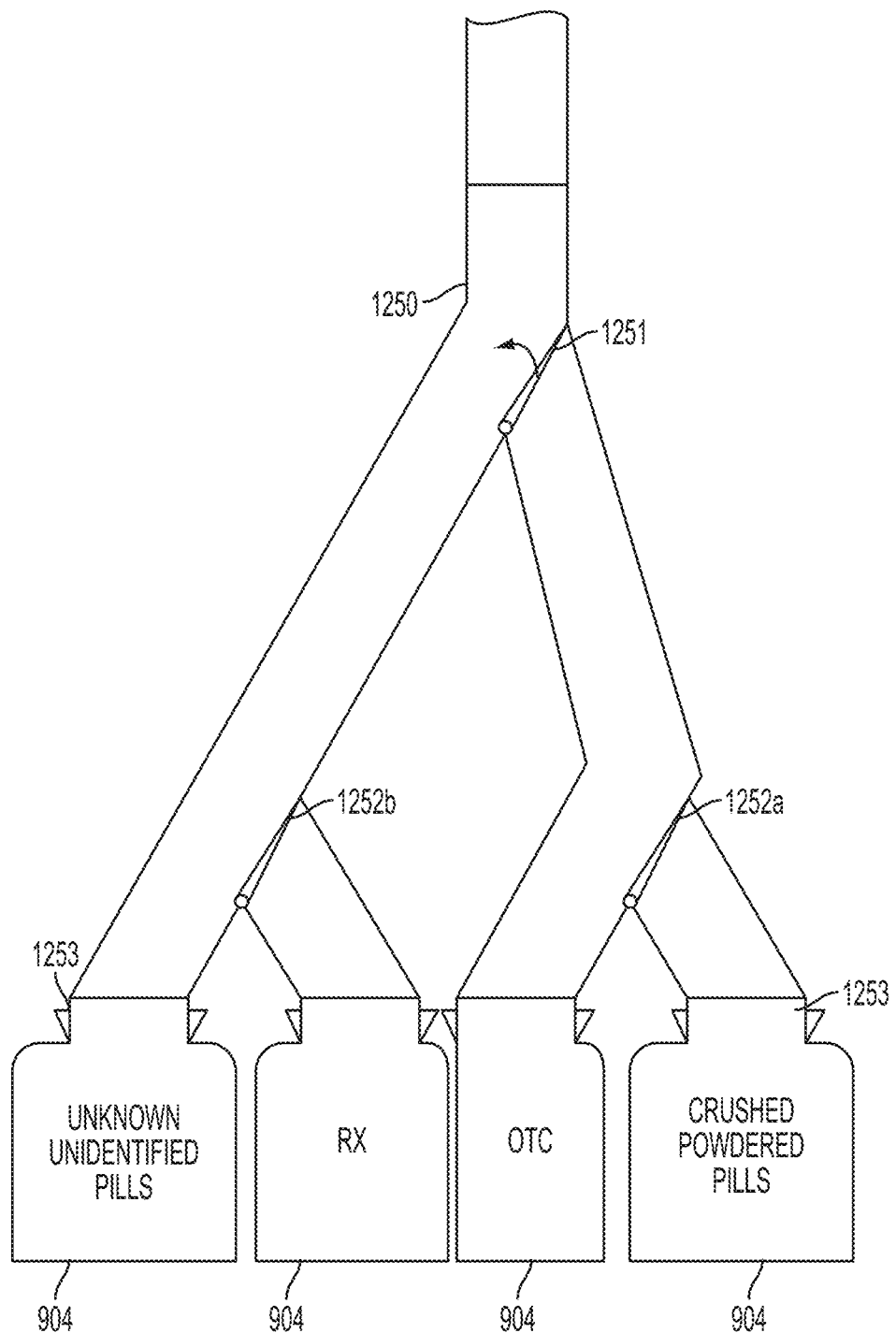
FIG. 19 illustrates an exemplary medicine distribution apparatus and collection bins of the medicine-processing machine which relies on a plurality of diverters to divert medicines between specific collection bins.

FIG. 19 illustrates a medicine distribution device 1250 which may be attached to each of the plurality of outlets 933a-e of the linear distribution manifold illustrated in FIG. 11B. The medicine distribution device 1250 includes a primary diverter 1251 and two secondary diverters 1252a and b. The medicine distribution device 1250 may include tertiary, quaternary, and so on, diverters to directing each medicine of a specific brand or identity to a specific collection bin. Additional imaging devices or sensors may be installed along the chutes of the medicine distribution device 1250 to track a medicine as it moves towards its correct collection bin. In one embodiment (FIG. 20), the medicine processing machine 1200 includes distribution belts or conveyors 1274 (FIG. 20) instead of the distribution device 1250 (FIG. 19) for achieving essentially the same result, delivering an identified medicine to a designated collection area 1278 (FIG. 20). The medicine distribution device, belt or conveyor may form a complex network of paths and diverters facilitating the distribution of hundreds or thousands of medicines to different collection bins where each bin may contain only a single type of medicine or medicines with the same active ingredients.

In an exemplary embodiment, the medicine distribution device 1250 (FIG. 19) has four outlets leading to collections bins 904 for unknown or unidentified medicines, prescription (RX) medicines, over the counter (OTC) medicines, and crushed or powdered medicines. The mounting mechanisms 1253 for attaching the medicine collection bins to the medicine distribution device can be of a variety of devices including a pivotal clamp, a sliding clamp, or a quick release fastener among others. The purpose of these mounting mechanisms 1253 is to physically attach the medicine collection bins 904 to the medicine distribution device 1250 while they are being filled with medicines. The controller 1240 (FIG. 18) can monitor the number medicines going into any given collection bin and stop the flow additional medicines to that bin if it is full. The controller can further display the bin being full on the display module 1250, actuate a mechanism for the filled collection bin to be automatically replaced by an empty bin, or automatically contact a service operator to come and replace the filled bin.

In some embodiments, if a collection bin is designated to receive, for example, medicines containing narcotics, the collection bin may include a deactivating agent (e.g., bleach) or an abuse-preventing agent to prevent the possibility of the medicines being stolen or abused from this bin. In another embodiment, the information about which bin contains what sorted medicines is kept secret or encrypted for preventing possible abuse. In this case, the collection bins have no markings other than bar codes that will be read at a collection facility by authorized personnel. This security process can be further enhanced by utilization of the media reader on the medicine-processing machine 1200. In one embodiment, only an authorized personnel who would first insert a card to the media reader slot 1252 (FIG. 20) on the machine, which identifies him or her as a particular authorized person, can obtain access to the inside of the machine.

In one embodiment, a medicine-processing machine of the subject technology acts as a drop box or a medicine deposition kiosk for receiving unused, expired or recalled medications, in particular, unused solid and semisolid oral dosage forms. It may further be configured to accept syrups and ampules or any other un-used, expired, recalled or partially used medications safely and securely. In an embodiment where the medicine-processing machine of the subject technology acts as a drop box, it is configured to separate medicines into Rx (prescription medication), OTC (over the counter medication) or unknown/unidentified. The Rx and OTC medicines will then be transported to a medication recycling facility where the medicines are separate based on, for example, their active ingredients. The unknown/unidentified medicines will be identified in a lab, and their information will be added to the reference medicine image database/storage 31/510 (FIG. 1 or 7, respectively), which will facilitate the identification of these medicines at a later date. In another embodiment, the medicine processing machine has means for controlling the temperature of the collection bins/storage area of the machine. In another embodiment, the medicine processing machine of the subject technology has means for keeping any residual medication particles or dust inside the medicine processing machine. In this case, the machine includes a vacuum or suctioning means for pulling the air from outside in and passing it through a hepa filter before sending the air out. This air suctioning and filtration action ensures that no residual particles or dust from medicines are discharged from the medicine processing machine. In another embodiment, the medicine processing machine, in return for depositing unused medicines, generates coupons or receipts that can be redeemed for cash or for receiving discounts at a store. In another embodiment, the medicine processing machine or kiosk allows the user to access their medicine deposit history on the machine's display unit or online via a computer or a smart mobile phone.

In another embodiment, the medicine processing machine of the subject technology includes a plurality of sorters 1000, medicine identification chambers 21 and distribution mechanisms which are installed in parallel or in series (e.g., in cascade), which will allow for the identification and sorting of thousands of medicines.

FIG. 20 illustrates an exemplary medicine sorting and storage system or device in which loose, mixed medicines 1262 are introduced to the system by placing them on the surface 1262 to which shaker/vibrator 1265 is attached for facilitating the movement and feeding of the medicines into the identification and sorting device. At the bottom of surface 1260 a conveyor belt 1264 picks the medicines and carries them upward for delivery into a medicine identification chamber 1270. The conveyor belt 1264 in the areas where medicines are carried has edges 1267 on both sides (to form a groove) to prevent the medicines from falling off the conveyor belt. The conveyor belt may have multiple medicine carrying grooves ending in multiple medicine identification chambers 1270. In an embodiment, the width of these grooves is between 2-15 cm or slightly wider than the largest medicine to be carried in them. In addition to the edges 1267, plate 1268 may be installed above the conveyor belt to prevent medicines 1262 from pouring on and interfering with the medicines that are moving on the belt 1264. The plate 1268 may have an edge 1266 that prevents the balk medicines to get on the conveyor belt. Rather, the edge 1266 causes medicines to move individually as much as possible or in a single file along the path towards the medicine identification chamber. In addition, both the conveyor belt 1264 and the plate 1268 have shakers or vibrators 1265 to cause the medicine to separate from one another and move individually on the belt. The shaking or vibration urges the piggybacked medicines to disengage from one another and to move in a single file and behind each other as they move towards the medicine identification chamber.

Once the medicines are passed through the medicine identification chamber 1270 and are identified, they are transferred onto conveyor belt 1272 to be distributed or sorted to their desired containers. The controller 1261 (which functions similar to controller 1240 in FIG. 18) ensures that proper diverters 1275 open to route each medicine to its designated bin or container 1278. Additional imaging devices or sensors may be installed along conveyor belt 1272 to track a medicine as it moves towards its correct collection bin 1278. Each diverter is actuated by motor 1273 and the belt has edges 1274 to prevent medicines from falling off the conveyor belt. In one embodiment, the medicines to be identified and sorted may be bottles of liquid medicines (e.g., syrups). In this case, the conveyor belt 1264 is placed be horizontal and the medicine identification chamber is designed such that the conveyor belt passes through it while carrying the bottles to be identified. The device may further include a robotic bottle-opener and a robotic arm to pour the liquid medicines in appropriate containers once they are identified.

Example I

Separating Hazardous Drugs from Mixture of Drugs

Large quantities of mixed medicines accumulate daily at nursing home, a hospital and doctors office or pharmaceutical companies. A lot of these medicines may not be necessarily hazardous but the possibility that they may have been mixed with hazardous medicines is high. The method and device of the subject technology allows for identification and separation of hazardous medicines from non-hazardous ones. This separation facilitates the proper disposal of these hazardous medicines and helps reducing the adverse impact of these medicines on the environment and human health.

Thus, in this example, the device of the subject technology is configured to separate hazardous medicines from non-hazardous ones. Exemplary hazardous medicines are listed in Table 4 below (which is a reproduction of the NIOSH List of hazardous medicines announced by the U.S. National Institute for Occupational Safety and Health in 2012). The information about the physical (including their shapes, colors, surface lines, imprints, markings, debosses, embosses, grooves, writing or etc.) and chemical features of these medicines as well as their images are collected and stored in the system (e.g., the image processing unit or the reference image database) of the subject technology. Preferably, the medicine identification chamber or unit of the subject technology is used to generate multiple reference images for each of these medicines. In accordance to the method and device of the subject technology, a target medicine is then processed for identification by comparing its digital image(s) with the digital images of the reference medicines.

Upon introduction of medicines to the device of the subject technology, hazardous medicines are quickly identified and separated from the non-hazardous medicines. The hazardous medicines are then subjected to proper disposal while the non-hazardous medicines can be shipped to landfills.

TABLE 4

Sample List of Drugs that Should be Handled as Hazardous

| Drug | Source | AHFS Pharmacologic-therapeutic classification |
| --- | --- | --- |
| Acitretin | 7 | 88:04 Vitamin A |
| Aldesleukin | 4, 5 | 10:00 Antineoplastic agents |
| Ambrisentan | 7 | 24:12.92 Vasodilating agents, miscellaneous |
| Alefacept | 6 | 84:92 Skin and mucous membrane agents, miscellaneous |
| Alitretinoin | 3, 4, 5 | 84:92 Skin and mucous membrane agents, miscellaneous |
| Altretamine | 1, 2, 3, 4, 5 | 10:00 Antineoplastic agents |
| Amsacrine | 3, 5 | Not in AHFS (antineoplastic agent) |
| Anastrozole | 1, 5 | 10:00 Antineoplastic agents |
| Arsenic trioxide | 1, 2, 3, 4, 5 | 10:00 Anti neoplastic agents |
| Asparaginase | 1, 2, 3, 4, 5 | 10:00 Antineoplastic agents |
| Azacitidine | 3, 5 | 10:00 Anti neoplastic agents |
| Azathioprine | 2, 3, 5 | 92:44 Immunosuppressant agents |
| *Bacillus* Calmette-Guerin (BCG) | 1, 2, 4 | 80:12 Vaccines |
| Bendamustine HCl | 7 | 10:00 Antineoplastic agents |
| Bexarotene | 2, 3, 4, 5 | 10:00 Anti neoplastic agents |
| Bicalutamide | 1, 5 | 10:00 Anti neoplastic agents |
| Bleomycin | 1, 2, 3, 4, 5 | 10:00 Antineoplastic agents |
| Bortezomib | 6 | 10:00 Antineoplastic agents |
| Bosentan | 6 | 24:12.92 Vasodilating agents, miscellaneous |
| Busulfan | 1, 2, 3, 4, 5 | 10:00 Antineoplastic agents |
| Cabergoline | 7 | 28:36.20.04 Ergot-derivative dopamine receptor agonists |
| Capecitabine | 1, 2, 3, 4, 5 | 10:00 Antineoplastic agents |
| Carbamazepine | 7 | 28:12.92 Anticonvulsants, miscellaneous |
| Carboplatin | 1, 2, 3, 4, 5 | 10:00 Antineoplastic agents |
| Carmustine | 1, 2, 3, 4, 5 | 10:00 Antineoplastic agents |
| Cetrorelix acetate | 5 | 92:40 Gonadotropin-releasing hormone antagonists |
| Chlorambucil | 1, 2, 3, 4, 5 | 10:00 Antineoplastic agents |
| Chloramphenicol | 1, 5 | 8:12.08 Chloramphenicols |
| Choriogonadotropin alfa | 5 | 68:18 Gonadotropins |
| Cidofovir | 3, 5 | 8:18.32 Nucleosides and nucleotides |
| Cisplatin | 1, 2, 3, 4, 5 | 10:00 Antineoplastic agents |
| Cladribine | 1, 2, 3, 4, 5 | 10:00 Antineoplastic agents |
| Clofarabine | 6 | 10:00 Antineoplastic agents |
| Clonazepam | 7 | 28:12.08 Benzodiazepines |
| Colchicine | 5 | 92:16 Antigout agents |
| Cyclophosphamide | 1, 2, 3, 4, 5 | 10:00 Antineoplastic agents |
| Cyclosporin | 1 | 92:44 Immunosuppressive agents |
| Cytarabine | 1, 2, 3, 4, 5 | 10:00 Antineoplastic agents |
| Dacarbazine | 1, 2, 3, 4, 5 | 10:00 Anti neoplastic agents |
| Dactinomycin | 1, 2, 3, 4, 5 | 10:00 Anti neoplastic agents |
| Dasatinib | 6 | 10:00 Antineoplastic agents |
| Daunorubicin HCl | 1, 2, 3, 4, 5 | 10:00 Antineoplastic agents |
| Decitibine | 6 | 10:00 Antineoplastic agents |
| Degarelix | 7 | 10:00 Anti neoplastic agents |
| Denileukin | 3, 4, 5 | 10:00 Antineoplastic agents |
| Diethylstilbestrol | 5 | Not in AHFS (nonsteroidal synthetic estrogen) |
| Dinoprostone | 5 | 76:00 Oxytocics |
| Docetaxel | 1, 2, 3, 4, 5 | 10:00 Antineoplastic agents |
| Doxorubicin | 1, 2, 3, 4, 5 | 10:00 Antineoplastic agents |
| Dronedarone HCl | 7 | 24:04.04 Antiarrythmics |
| Dutasteride | 5 | 92:08 5-alpha reductase inhibitors |
| Entecavir | 6 | 8:18.32 Nucleosides and nucleotides |
| Epirubicin | 1, 2, 3, 4, 5 | 10:00 Antineoplastic agents |

TABLE 4-continued

Sample List of Drugs that Should be Handled as Hazardous

| Drug | Source | AHFS Pharmacologic-therapeutic classification |
| --- | --- | --- |
| Ergonovine/ methylergonovine | 5 | 76:00 Oxytocics |
| Estradiol | 1, 5 | 68:16.04 Estrogens |
| Estramustine phosphate | 1, 2, 3, 4, 5 | 10:00 Antineoplastic agents |
| Estrogen-progestin combinations | 5 | 68:12 Contraceptives |
| Estrogens, conjugated | 5 | 68:16.04 Estrogens |
| Estrogens, esterified | 5 | 68:16.04 Estrogens |
| Estrone | 5 | 68:16.04 Estrogens |
| Estropipate | 5 | 68:16.04 Estrogens |
| Etoposide | 1, 2, 3, 4, 5 | 10:00 Antineoplastic agents |
| Everolimus | 7 | 10:00 Anti neoplastic agents |
| Exemestane | 1, 5 | 10:00 Antineoplastic agents |
| Finasteride | 1, 3, 5 | 92:08 5-alpha reductase inhibitors |
| Floxuridine | 1, 2, 3, 4, 5 | 10:00 Antineoplastic agents |
| Fludarabine | 1, 2, 3, 4, 5 | 10:00 Antineoplastic agents |
| Fluorouracil | 1, 2, 3, 4, 5 | 10:00 Anti neoplastic agents |
| Fluoxymesterone | 5 | 68:08 Androgens |
| Flutamide | 1, 2, 5 | 10:00 Antineoplastic agents |
| Fulvestrant | 5 | 10:00 Antineoplastic agents |
| Ganciclovir | 1, 2, 3, 4, 5 | 8:18.32 Nucleosides and nucleotides |
| Ganirelix acetate | 5 | 92:40 Gonadotropin-releasing hormone antagonists |
| Gemcitabine | 1, 2, 3, 4, 5 | 10:00 Antineoplastic agents |
| Gemtuzumab ozogamicin | 1, 3, 4, 5 | 10:00 Antineoplastic agents |
| Gonadotropin, chorionic | 5 | 68:18 Gonadotropins |
| Goserelin | 1, 2, 5 | 10:00 Antineoplastic agents |
| Hydroxyurea | 1, 2, 3, 4, 5 | 10:00 Antineoplastic agents |
| Idarubicin | 1, 2, 3, 4, 5 | 10:00 Antineoplastic agents |
| Ifosfamide | 1, 2, 3, 4, 5 | 10:00 Antineoplastic agents |
| Imatinib mesylate | 1, 3, 4, 5 | 10:00 Antineoplastic agents |
| Irinotecan HCl | 1, 2, 3, 4, 5 | 10:00 Antineoplastic agents |
| Ixabepilone | 7 | 10:00 Anti neoplastic agents |
| Leflunomide | 3, 5 | 92:36 Disease modifying antirheumatic agents |
| Lenalidomide | 6 | 92:20 Biologic response modifiers |
| Letrozole | 15 | 10:00 Antineoplastic agents |
| Leuprolide acetate | 1, 2, 5 | 10:00 Antineoplastic agents |
| Lomustine | 1, 2, 3, 4, 5 | 10:00 Antineoplastic agents |
| Mechlorethamine | 1, 2, 3, 4, 5 | 10:00 Antineoplastic agents |
| Medroxyprogesterone acetate | 6 | 68:32 Progestins |
| Megestrol | 1, 5 | 10:00 Antineoplastic agents |
| Melphalan | 1, 2, 3, 4, 5 | 10:00 Antineoplastic agents |
| Menotropins | 5 | 68:18 Gonadotropins |
| Mercaptopurine | 1, 2, 3, 4, 5 | 10:00 Antineoplastic agents |
| Methotrexate | 1, 2, 3, 4, 5 | 10:00 Anti neoplastic agents |
| Methyltestosterone | 5 | 68:08 Androgens |
| Mifepristone | 5 | 76:00 Oxytocics |
| Mitomycin | 1, 2, 3, 4, 5 | 10:00 Antineoplastic agents |
| Mitotane | 1, 4, 5 | 10:00 Antineoplastic agents |
| Mitoxantrone HCl | 1, 2, 3, 4, 5 | 10:00 Antineoplastic agents |
| Mycophenolate mofetil | 1, 3, 5 | g2:44 Immunosuppressive agents |
| Mycophenolic acid | 7 | 92:44 Immunosuppressive agents |
| Nafarelin | 5 | 68:18 Gonadotropins |
| Nelarabine | 6 | 10:00 Antineoplastic agents |
| Nilotinib | 7 | 10:00 Anti neoplastic agents |
| Ni lutamide | 1, 5 | 10:00 Antineoplastic agents |
| Oxaliplatin | 1, 3, 4, 5 | 10:00 Antineoplastic agents |
| Oxcarbazepine | 7 | 28:12.92 Anticonvulsants, miscellaneous |
| Oxytocin | 5 | 76:00 Oxytocics |
| Paclitaxel | 1, 2, 3, 4, 5 | 10:00 Antineoplastic agents |
| Palifermin | 6 | 84:16 Cell stimulants and proliferants |
| Paroxetine** | 6, 7 | 28:16.04.20 Selective serotonin uptake inhibitors |
| Pazopanib HCl | 7 | 10:00 Antineoplastic agents |
| Pegaspargase | 1, 2, 3, 4, 5 | 10:00 Anti neoplastic agents |
| Pemetrexed | 6 | 10:00 Antineoplastic agents |
| Pentamidine isethionate | 1, 2, 3, 5 | 8:30.92 Antiprotozoals, miscellaneous |
| Pentetate calcium trisodium†† | 6 | Not in AHFS |
| Pentostatin | 1, 2, 3, 4, 5 | 10:00 Antineoplastic agents |
| Phenoxybenzamine HCl | 7 | 12:16.04.04 Non-selective alpha-adrenergic blocking agents |
| Pipobroman | 3, 5 | Not in AHFS (antineoplastic agent) |
| Plerixafor | 7 | 20:16 Hematopoietic agents |
| Podofilox | 5 | 84:92 Miscellaneous skin and mucous membrane agents (mitotic inhibitor) |
| Podophyllum resin | 5 | 84:92 Skin and mucous membrane agents, miscellaneous |

TABLE 4-continued

Sample List of Drugs that Should be Handled as Hazardous

| Drug | Source | AHFS Pharmacologic-therapeutic classification |
|---|---|---|
| Pralatrexate | 7 | 10:00 Antineoplastic agents |
| Procarbazine | 1, 2, 3, 4, 5 | 10:00 Antineoplastic agents |
| Progesterone | 5 | 68:32 Progestins |
| Progestins | 5 | 68:12 Contraceptives |
| Raloxifene | 5 | 68:16.12 Estrogen agonists-antagonists |
| Rasagiline mesylate | 6 | 28:36 Antiparkinsonian agents |
| Ribavirin | 1, 2, 5 | 8:18.32 Nucleosides and nucleotides |
| Risperidone | 6 | 28:16.08.04 Atypical antipsychotics |
| Romidepsin | 7 | 10:00 Antineoplastic agents |
| Sirolimus | 6 | 92:44 Immunosuppressive agents |
| Sorafenib | 6 | 10:00 Antineoplastic agents |
| Streptozocin | 1, 2, 3, 4, 5 | 10:00 Antineoplastic agents |
| Sunitinib malate | 6 | 10:00 Antineoplastic agents |
| Tacrolimus | 1, 5 | 92:44 Immunosuppressive agents |
| Tamoxifen | 1, 2, 5 | 10:00 Antineoplastic agents |
| Televancin | 7 | 8:12.28.16 Glycopeptides |
| Temozolomide | 3, 4, 5 | 10:00 Antineoplastic agents |
| Temsirolimus | 7 | 10:00 Antineoplastic agents |
| Teniposide | 1, 2, 3, 4, 5 | 10:00 Antineoplastic agents |
| Testolactone | 5 | 10:00 Antineoplastic agents |
| Testosterone | 5 | 68:08 Androgens |
| Tetracycline HCl | 7 | 8:12.24 Tetracyclines |
| Thalidomide | 1, 3, 5 | 92:20 Biologic response modifiers |
| Thioguanine | 1, 2, 3, 4, 5 | 10:00 Antineoplastic agents |
| Thiotepa | 1, 2, 3, 4, 5 | 10:00 Antineoplastic agents |
| Topotecan | 1, 2, 3, 4, 5 | 10:00 Antineoplastic agents |
| Toremifene citrate | 1, 5 | 10:00 Antineoplastic agents |
| Tretinoin | 1, 2, 3, 5 | 84:16 Cell stimulants and proliferants |
| Trifluridine | 1, 2, 5 | 52:04.20 Antivirals |
| Triptorelin | 5 | 10:00 Anti neoplastic agents |
| Uracil mustard | 3, 5 | Not in AHFS (antineoplastic agent) |
| Valganciclovir | 1, 3, 5 | 8:18.32 Nucleosides and nucleotides |
| Valproic acid/ divalproex Na | 7 | 28:12.92 Anticonvulsants, miscellaneous |
| Valrubicin | 1, 2, 3, 5 | 10:00 Antineoplastic agents |
| Vidarabine | 1, 2, 5 | Not in AHFS |
| Vigabatrin | 7 | 28:12.92 Anticonvulsants, miscellaneous |
| Vinblastine sulfate | 1, 2, 3, 4, 5 | 10:00 Antineoplastic agents |
| Vincristine sulfate | 1, 2, 3, 4, 5 | 10:00 Antineoplastic agents |
| Vinorelbine tartrate | 1, 2, 3, 4, 5 | 10:00 Antineoplastic agents |
| Vorinostat | 6 | 10:00 Antineoplastic agents |
| Zidovudine | 1, 2, 5 | 8:18:08 Antiretroviral agents |
| Ziprasidone HCl | 7 | 28:16.08.04 Atypical antipsychotics |
| Zoledronic acid | 7 | 92:24 Bone resorption inhibitors |
| Zonisamide | 6 | 28:12.92 Anticonvulsants, miscellaneous |

1. The NIH Clinical Center, Bethesda, MD (Revised August 2002). The NIH Health Clinical Center Hazardous Drug (HD) list is part of the NIH Clinical Center's hazard communication program. It was developed in compliance with the OSHA hazard communication standard [29 CFR 1910.1200] as it applies to hazardous drugs used in the workplace. The list is continually revised and represents the diversity of medical practice at the NIH Clinical Center; however, its content does not reflect an exhaustive review of all FDA-approved medications that may be considered hazardous, and it is not intended for use outside the NJH.

2. The Johns Hopkins Hospital, Baltimore, MD (Revised September 2002).

3. The Northside Hospital, Atlanla, GA (Revised August 2002).

4. The University of Michigan Hospitals and Health Centers. Ann Arbor, MI (Revised February 2003)

5. This sample listing of hazardous drugs was compiled by the Pharmaceutical Research and Manufacturers of America (PhRMA) using information from the AHFS DI monographs published by ASHP in selected AHFS Pharmacologic-Therapeutic Classification categories [ASHP/AHFS DI 2003] and applying the definition for hazardous drugs. The list also includes drugs from other sources that satisfy the definition for hazardous drugs [PDR 2004; Sweetman 2002; Shepard 2001; Schardein 2000; REPROTOX 2003]. Newly approved drugs that have structures or toxicological profiles that mimic the drugs on this list should also be included. This list was revised in June 2004.

6. NIOSH addition 2010 updated using ASHP/AHFS DI 2010.

7. NIOSH addition 2012 updated using ASHP/AHFS DI 2011.

**2010, Paroxetine HCl; 2012, Paroxetine mesylate

††Refers to non-radio-labeled formulation only.

Radio-Pharmaceuticals that are Regulated by Nuclear Regulatory Commission

| Drug | AHFS Pharmacologic-therapeutic classification |
| --- | --- |
| ibritumomab tiuxetan | 10:00 Antineoplastic agents |
| tositumomab | 10:00 Antineoplastic agents |

Drugs that are Currently not Available in the United States‡

| Drug | AHFS Pharmacologic-therapeutic classification |
| --- | --- |
| dienestrol | 68:16.04 Estrogens |
| interferon alfa n 1 | 10:00 Antineoplastic agents |
| perphosphamide | Not in AHFS (antineoplastic agent) |
| piritrexim isethionate | Not in AHFS (anti neoplastic agent) |
| plicamycin | Not in AHFS (anti neoplastic agent) |
| prednumustine | Not in AHFS (anti neoplastic agent) |
| raltitrexed | Not in AHFS (anti neoplastic agent) |
| trimetrexate glucuronate | 8:30.92 Miscellaneous antiprotozoals |
| vindesine | Not in AHFS (anti neoplastic agent) |

‡The NIOSH hazardous drug list is based on approvals by the U.S. FDA. These drugs are not approved by the U.S. FDA and are no longer available in the U.S. However, some may be available in other countries.

It is submitted that the subject technology has been shown and described in what is considered to be exemplary embodiments. It is recognized, however, that departures may be made within the scope of the subject technology and that obvious modifications will occur to a person skilled in the art. With respect to the above description then, it is to be realized that the optimum dimensional relationships for the parts of the subject technology, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present subject technology.

Therefore, the foregoing is considered as illustrative only of the principles of the subject technology. Further, since numerous modifications and changes will readily occur to those skilled in the art, it is not desired to limit the subject technology to the exact construction and operation shown and described, and accordingly, all suitable modifications and equivalents may be resorted to, falling within the scope of the subject technology.

What is claimed is:

1. A computer implemented method for sorting a plurality of different medicines, the method comprising the steps of (i) queuing the different medicines, wherein the queuing step comprises receiving and sorting the plurality of different medicines for identification, (ii) identifying the different medicines, after said queuing wherein the identifying step comprises an image capturing and an image processing for identifying each of the different medicines, (iii) sorting the different medicines, after said identifying wherein the sorting step comprises routing the identified medicines to separate locations.

2. The method of claim 1, wherein the image processing comprises a reference image database comprising reference images of the different medicines or reference images of at least a portion of each of the reference medicines or a combination thereof, wherein said portion comprises edges and lines or a physical feature comprising shape, color, surface line, imprint, marking, deboss, emboss, groove or writing.

3. The method of claim 2, wherein the image processing further comprises an algorithm for detecting, matching and/or classifying each of the different medicines based on the reference images.

4. The method of claim 3, wherein the algorithm comprises squared difference, normalized squared difference, cross correlation, normalized cross correlation, correlation coefficient, normalized correlation coefficient, neural network, Bayesian belief network, support vector machines, fuzzy logic, Hidden Markov model.

5. A device for sorting a plurality of different medicines, said device comprising a sorting an queuing unit for receiving and sorting the plurality of the different medicines for identification; an identification unit, wherein the identification unit comprises an image capturing and an image processing, for identifying each of the different medicines after said receiving and sorting; and a sorting unit for routing the identified different medicines to separate locations after said identification.

6. The device of claim 5, wherein the image processing comprises a reference image database comprising reference images of the different medicines or reference images of at least a portion of each of the reference medicines, wherein said portion comprises edges and lines or a physical feature comprising shape, color, surface line, imprint, marking, deboss, emboss, groove or writing.

7. The device of claim 6, wherein the image processing further comprises and an algorithm for detecting, matching and/or classifying each of the different medicines based on the reference images.

8. The device of claim 7, wherein the algorithm comprises squared difference, normalized squared difference, cross correlation, normalized cross correlation, correlation coefficient, normalized correlation coefficient, neural network, Bayesian belief network, support vector machines, fuzzy logic or Hidden Markov model.

9. A computer implemented method for separating hazardous and/or government regulated medicines from non-hazardous medicines, the method comprising the steps of (i) queuing the medicines, wherein the queuing step comprises receiving and sorting the medicines for identification, (ii) identifying the hazardous and/or government regulated medicines, after said queuing wherein the identifying step comprises an image capturing and an image processing for identifying each of the hazardous and/or government regulated medicines, (iii) sorting the hazardous and/or government regulated medicines, after said identifying wherein the sorting step comprises routing the identified hazardous and/or government regulated medicines to a separate location from the non-hazardous medicines for disposal.

10. The method of claim 9, wherein the image processing comprises a reference image database comprising reference images of the hazardous and/or government regulated medicines or reference images at least a portion of each of the hazardous and/or government regulated medicines or a combination thereof, wherein said portion comprises edges and lines or a physical feature comprising shape, color, surface line, imprint, marking, deboss, emboss, groove or writing.

11. The method of claim 10, wherein the image processing further comprises an algorithm for detecting, matching and/or classifying each of the hazardous and/or government regulated medicines based on the reference images.

12. The method of claim 11, wherein the algorithm comprises squared difference, normalized squared difference, cross correlation, normalized cross correlation, correlation coefficient, normalized correlation coefficient, neural network, Bayesian belief network, support vector machines, fuzzy logic or Hidden Markov model.

13. A device for separating hazardous and/or government regulated medicines from non-hazardous medicines, said device comprising a sorting and queuing unit for receiving and sorting the medicines for identification; an identification unit, wherein the identification unit comprises an image capturing and an image processing, for identifying each of the hazardous and/or government regulated medicines after said receiving and sorting; and a sorting unit for routing the identified hazardous and/or government regulated medicines to separate locations from the non-hazardous medicines for disposal after said identification.

14. The device of claim 13, wherein the image processing comprises a reference image database comprising reference images of the hazardous and/or government regulated medicines or reference images of at least a portion of each of the hazardous and/or government regulated medicines or a combination thereof, wherein said portion comprises edges and lines or a physical feature comprising shape, color, surface line, imprint, marking, deboss, emboss, groove or writing.

15. The device of claim 14, wherein the image processing further comprises an algorithm for detecting, matching and/or classifying each of the hazardous and/or government regulated medicines based on the reference images.

16. The device of claim 15, wherein the algorithm comprises squared difference, normalized squared difference, cross correlation, normalized cross correlation, correlation coefficient, normalized correlation coefficient, neural network, Bayesian belief network, support vector machines, fuzzy logic or Hidden Markov model.

* * * * *